(12) United States Patent
Chen

(10) Patent No.: US 9,919,979 B2
(45) Date of Patent: Mar. 20, 2018

(54) FERTILIZER-COMPATIBLE COMPOSITION

(75) Inventor: Chi-Yu R. Chen, Raleigh, NC (US)

(73) Assignee: Bayer CropScience LP, Research Triangle Park, NC (US)

( * ) Notice: Subject to any disclaimer, the term of this patent is extended or adjusted under 35 U.S.C. 154(b) by 1733 days.

(21) Appl. No.: 11/325,525

(22) Filed: Jan. 5, 2006

(65) Prior Publication Data

US 2006/0166898 A1   Jul. 27, 2006

Related U.S. Application Data

(63) Continuation-in-part of application No. 11/041,167, filed on Jan. 21, 2005, now abandoned.

(51) Int. Cl.

| | |
|---|---|
| *A01N 43/40* | (2006.01) |
| *C05G 3/02* | (2006.01) |
| *A01N 25/04* | (2006.01) |
| *A01N 37/26* | (2006.01) |
| *A01N 37/40* | (2006.01) |
| *A01N 37/50* | (2006.01) |
| *A01N 43/56* | (2006.01) |
| *A01N 43/653* | (2006.01) |
| *A01N 43/707* | (2006.01) |
| *A01N 43/80* | (2006.01) |
| *A01N 43/82* | (2006.01) |
| *A01N 47/02* | (2006.01) |
| *A01N 47/22* | (2006.01) |
| *A01N 47/24* | (2006.01) |
| *A01N 51/00* | (2006.01) |
| *A01N 53/00* | (2006.01) |
| *C05G 3/00* | (2006.01) |
| *C05G 3/06* | (2006.01) |

(52) U.S. Cl.
CPC .............. *C05G 3/02* (2013.01); *A01N 25/04* (2013.01); *A01N 37/26* (2013.01); *A01N 37/40* (2013.01); *A01N 37/50* (2013.01); *A01N 43/40* (2013.01); *A01N 43/56* (2013.01); *A01N 43/653* (2013.01); *A01N 43/707* (2013.01); *A01N 43/80* (2013.01); *A01N 43/82* (2013.01); *A01N 47/02* (2013.01); *A01N 47/22* (2013.01); *A01N 47/24* (2013.01); *A01N 51/00* (2013.01); *A01N 53/00* (2013.01); *C05G 3/007* (2013.01); *C05G 3/06* (2013.01)

(58) Field of Classification Search
CPC .... A01N 2300/00; A01N 25/04; A01N 37/26; A01N 37/40; A01N 37/50; A01N 43/40; A01N 43/56; A01N 43/653; A01N 43/707; A01N 43/80; A01N 43/82; A01N 47/02; A01N 47/22; A01N 47/24; A01N 51/00; A01N 53/00; C05G 3/007; C05G 3/02; C05G 3/06

USPC .................... 514/22, 340, 341, 357
See application file for complete search history.

(56) References Cited

U.S. PATENT DOCUMENTS

| | | | |
|---|---|---|---|
| 3,992,532 A | 11/1976 | Dimitri | 424/213 |
| 4,071,617 A | 1/1978 | Graves et al. | 424/78 |
| 4,236,579 A | 12/1980 | Kalfoglou | |
| 4,464,193 A | 8/1984 | Kaneko et al. | 71/83 |
| 4,531,002 A | 7/1985 | Harris | 544/54 |
| 4,590,272 A | 5/1986 | Shiokawa et al. | 544/335 |
| 4,606,862 A | 8/1986 | Harris | 260/402.5 |
| 4,647,570 A | 3/1987 | Shiokawa et al. | 514/341 |
| 4,678,795 A | 7/1987 | Shiokawa et al. | 514/341 |
| 4,680,294 A | 7/1987 | Shiokawa et al. | 514/256 |
| 4,687,845 A | 8/1987 | Hollowood et al. | 544/54 |
| 4,742,060 A | 5/1988 | Shiokawa et al. | 514/252 |
| 4,772,620 A | 9/1988 | Shiokawa et al. | 514/341 |
| 4,774,247 A | 9/1988 | Shiokawa et al. | 514/256 |
| 4,803,277 A | 2/1989 | Shiokawa et al. | 514/332 |
| 4,806,553 A | 2/1989 | Shiokawa et al. | 514/332 |
| 4,812,454 A | 3/1989 | Shiokawa et al. | 514/256 |
| 4,812,571 A | 3/1989 | Shiokawa et al. | 546/296 |
| 4,845,106 A | 7/1989 | Shiokawa et al. | 514/342 |
| 4,849,432 A | 7/1989 | Shiokawa et al. | 514/341 |
| 4,882,344 A | 11/1989 | Shiokawa et al. | 514/342 |
| 4,914,113 A | 4/1990 | Shiokawa et al. | 514/333 |
| 4,918,086 A | 4/1990 | Gsell | 514/351 |
| 4,918,088 A | 4/1990 | Gsell | 514/357 |
| 4,948,798 A | 8/1990 | Gsell | 514/275 |
| 4,963,572 A | 10/1990 | Gsell | 514/357 |
| 4,963,574 A | 10/1990 | Bachmann et al. | 514/357 |
| 4,988,712 A | 1/1991 | Shiokawa et al. | 514/340 |
| 5,001,138 A | 3/1991 | Shiokawa et al. | 514/342 |
| 5,032,589 A | 7/1991 | Shiokawa et al. | 514/245 |
| 5,034,404 A | 7/1991 | Uneme et al. | 514/365 |
| 5,034,524 A | 7/1991 | Shiokawa et al. | 544/124 |
| 5,039,686 A | 8/1991 | Davies et al. | 514/341 |
| 5,049,571 A | 9/1991 | Gsell | 514/345 |
| 5,051,434 A | 9/1991 | Kozo et al. | 514/357 |
| 5,063,236 A | 11/1991 | Gsell | 514/318 |

(Continued)

FOREIGN PATENT DOCUMENTS

| | | |
|---|---|---|
| DE | 36 39 877 A1 | 5/1988 |
| DE | 37 12 307 A1 | 10/1988 |

(Continued)

OTHER PUBLICATIONS

Rutland, Fertilizer Research, 1991,Kluwer Academic Publishers,30:99-114.*

(Continued)

*Primary Examiner* — Johann R Richter
*Assistant Examiner* — Courtney A Brown

(57) ABSTRACT

This invention relates to compositions compatible with liquid fertilizers and methods of use thereof.

23 Claims, No Drawings

(56) References Cited

U.S. PATENT DOCUMENTS

| | | | |
|---|---|---|---|
| 5,066,808 A | 11/1991 | Shiokawa et al. | 514/231.5 |
| 5,084,467 A | 1/1992 | Shiokawa et al. | 514/357 |
| 5,166,164 A | 11/1992 | Nanjo et al. | 514/357 |
| 5,175,301 A | 12/1992 | Minamida et al. | 546/272 |
| 5,192,778 A | 3/1993 | Kodaka et al. | 514/341 |
| 5,204,359 A | 4/1993 | Shiokawa et al. | 514/332 |
| 5,204,360 A | 4/1993 | Shiokawa et al. | 514/342 |
| 5,214,152 A | 5/1993 | Minamida et al. | 548/181 |
| 5,226,945 A | 7/1993 | Frisch | 504/148 |
| 5,238,949 A | 8/1993 | Shiokawa et al. | 514/327 |
| 5,240,626 A | 8/1993 | Thakur et al. | |
| 5,256,679 A | 10/1993 | Minamida et al. | 514/357 |
| 5,264,584 A | 11/1993 | Kodaka et al. | 548/332.5 |
| 5,280,123 A | 1/1994 | Nanjo et al. | 548/111 |
| 5,298,507 A | 3/1994 | Shiokawa et al. | 514/256 |
| 5,304,566 A | 4/1994 | Ishimitsu et al. | 514/357 |
| 5,384,324 A | 1/1995 | Shiokawa et al. | 514/365 |
| 5,405,961 A | 4/1995 | Nanjo et al. | 544/243 |
| 5,428,032 A | 6/1995 | Shiokawa et al. | 514/226.8 |
| 5,461,167 A | 10/1995 | Shiokawa et al. | 548/202 |
| 5,516,747 A | 5/1996 | Lachut | 504/116 |
| 5,547,918 A * | 8/1996 | Newton et al. | 504/361 |
| 5,580,889 A | 12/1996 | Shiokawa et al. | 514/343 |
| 5,612,358 A | 3/1997 | Ishimitsu et al. | 514/357 |
| 5,696,256 A | 12/1997 | Kando et al. | 540/463 |
| 5,719,146 A | 2/1998 | Shiokawa et al. | 514/229.2 |
| RE35,811 E | 5/1998 | Shiokawa et al. | 514/357 |
| 5,750,704 A | 5/1998 | Shiokawa et al. | 546/275.1 |
| 5,763,364 A | 6/1998 | Frisch et al. | 504/116 |
| 5,804,591 A * | 9/1998 | Valcke et al. | 514/383 |
| 5,849,768 A | 12/1998 | Minamida et al. | 514/357 |
| 5,852,012 A | 12/1998 | Maienfisch et al. | 514/229.2 |
| 5,935,981 A | 8/1999 | Minamida et al. | 514/365 |
| 6,022,871 A | 2/2000 | Maienfisch et al. | 514/229.2 |
| 6,022,967 A | 2/2000 | Shiokawa et al. | 544/298 |
| 6,124,297 A | 9/2000 | Minamida et al. | 514/255 |
| 6,160,126 A | 12/2000 | Kando et al. | 548/477 |
| 6,187,773 B1 | 2/2001 | Wu et al. | 514/245 |
| 6,232,309 B1 | 5/2001 | Shiokawa et al. | 514/222.5 |
| 6,297,374 B1 | 10/2001 | Shiokawa et al. | 544/55 |
| 6,344,453 B1 | 2/2002 | Shiokawa et al. | 514/223.8 |
| 6,376,487 B1 | 4/2002 | Maienfisch et al. | 514/229.2 |
| 6,407,248 B1 | 6/2002 | Minamida et al. | 546/331 |
| 6,627,753 B1 | 9/2003 | Maienfisch et al. | 544/67 |
| 7,238,645 B1 | 7/2007 | Chow et al. | |
| 7,307,043 B2 * | 12/2007 | Schlatter et al. | 504/100 |
| 7,504,362 B2 * | 3/2009 | Doiler et al. | 504/282 |
| 2001/0046994 A1 | 11/2001 | Wu et al. | 514/241 |
| 2002/0039971 A1* | 4/2002 | Hayashi et al. | 504/313 |
| 2003/0232821 A1 | 12/2003 | Maienfisch et al. | 514/229.2 |
| 2004/0020409 A1* | 2/2004 | Xiao et al. | 106/277 |
| 2006/0009535 A1* | 1/2006 | Wantling | 516/43 |
| 2008/0171820 A9* | 7/2008 | Sophiea et al. | 524/445 |

FOREIGN PATENT DOCUMENTS

| | | |
|---|---|---|
| EP | 0 498 231 A1 | 8/1992 |
| EP | 1213962 B1 | 2/2004 |
| JP | 63-287764 | 11/1988 |
| JP | 63-307857 | 12/1988 |
| JP | 2-207083 | 8/1990 |
| JP | 3-220176 | 9/1991 |
| JP | 3-246283 | 11/1991 |
| JP | 3-255072 | 11/1991 |
| JP | 3-279359 | 12/1991 |
| JP | 2002-284602 A1 * | 10/2002 |
| WO | 91/17659 | 11/1991 |
| WO | 95/01944 | 1/1995 |
| WO | 97/20462 | 6/1997 |

OTHER PUBLICATIONS

Krogh et al.,Chemosphere,vol. 50, Issue 7, Feb. 2003, pp. 871-901.*
Substantial. (2014). In merriam-webster.com. Retrieved Feb. 9, 2014, from: http://www.merriam-webster.com/dictionary/substantial.*
Database WPI Section Ch, Week 199425 Derwent Publications Ltd., London, GB; Class A97, AN 1994-206269 XP002383557 & JP 06 144975 A (Asahi Kako KK) May 24, 1994 (May 24, 1994) abstract.
Database WPI Section Ch, Week 200425 Derwent Publications Ltd., London, GB; Class A97, AN 2004-260130 XP002383558 & JP 2003 321303 A (Sumitomo Chem Co Ltd) Nov. 11, 2003 (Nov. 11, 2003) abstract.
Database WPI Section Ch, Week 200425 Derwent Publications Ltd., London, GB; Class A97, AN 2004 260129 XP002383559 & JP 2003 321302 A (Sumitomo Chem Co Ltd) Nov. 11, 2003 (Nov. 11, 2003) abstract.
Database WPi Section Ch, Week 199313 Derwent Publications Ltd., London, GB; Class A97, AN 1993-104144 XP002383560 & JP 05 043401 A (Nissan Chem Ind Ltd) Feb. 23, 1993 (Feb. 23, 1993) abstract.
Database WPI Section Ch, Week 200328 Derwent Publications Ltd., London, GB; Class A97, AN 2003-282031 XP002383561 & JP 2002 284602 A (Takeda Chem. Ind Ltd) Oct. 3, 2002 (Oct. 3, 2002) abstract.
"Admire Pro Systemic Protectant: Product Information"; Bayer Cropscience; http://www.bayercropscienceus.com/products_and_seeds/insecticides/admire.htm1; 16 Pages; Accessed on Aug. 18, 2010.
"Pest Management-Pesticides and Their Application-Compatibility of Pesticides"; Penn State University; http://agguide.agronomy.psu.edu/pm/sec1/sec110.cfm; 2 Pages; Accessed on Aug. 3, 2010.
Tank Mixing Herbicides and Fertilizers; Grounds Maintenance; http://grounds-mag.com/mag/grounds_maintenance_dos_donts_tankmixin/; 4 Pages; Accessed on Aug. 3, 2010.
"The Condensed Chemical Dictionary"; 10th Edition, by Gessner G. Hawley; Van Nostrand Reinhold Company Inc.; pp. 615 and 986; 1981.
P. J. Mulqueen; "Surfactants for Agrochemical Formulation" Industrial Applications of Surfactants II; Edited by D. R. Karsa, Royal Society of Chemistry, pp. 276-302; 1989.
Borregaard-Agricultural Chemicals; Borregaard Lignotech; http://www.denomega.com/eway/default.aspx?pid=232&trg=leftpage_6839&mainpage_6746=6; 2 Pages, Accessed on Aug. 18, 2010.
"The Organic Chemistry of Surfactants" in "Surfactants Science and Technology," by Drew Myers, VCH Publishers; pp. 26-79; 1988.
"Suspension Concentrates"; Unido; Workshop on Production of User and Environment Friendly Pesticide Formulations, Quality Assurance and Instrumental Methods of Analysis, Delhi, India, pp. 81-89; Mar. 2-9, 2009.
"Lignin"; Kirk-Othmer Encyclopedia of Chemical Technology; S. E. Lebo et al.; John Wiley & Sons; pp. 1-32; 2001.
Lignosulfonates Kemi Swedish Chemicals Agency; http://apps.kemi.se/flodessok/floden/kemamne_en/lignosulfonater_eng.htm; Aug. 2010.
Hans Mollet & Arnold Grubenmann; Translated by H. R. Payne "Formulation Technology," Wiley-VCH, Weiheim, Germany; pp. 177-178; 2001.
Dave Schuster, "Admire Pro Systemic Protectant", Group 4A Insecticide, 2009; pp. 1-7.
Gene Burgess "Tobacco Insects", Tabacco In-Service Training, Mar. 6, 2009; pp. 1-10.
Darwin Blue Speedwell "Controlling Pests & Deseases", gardenguides.com, 2009, pp. 1-4, Accessed on Jun. 17, 2011.
Gessner G. Hawley, "Distearyl Thiodipropionate", The Condensed Chemical Dictionary, Ninth Edition, Van Nostrand Reinhold Company, 1905-QD5.C5 1976, pp. 1-3.
"Pesticide Dictionary", Farm Chemicals Handbook, (2001), p. C11.
Jerry Gargulak, Letter Regarding Surface Tension of Sodium Lignosulfonate Compared to Common Surfactants, Borregaard Lignotech, Jun. 13, 2011, pp. 1-2.
Bissari et al. "Chemical Economics Handbook", Published Jan. 2009, Accessed on Apr. 29, 2011, p. 1.

(56) References Cited

OTHER PUBLICATIONS

Lignin Institute, www.lignin.org/whatis.html, Oct. 28, 2008; p. 2.
Encyclopedia "Lignosulfonates", http://en.wikipedia.org/wiki/lignosulfonates, Last Modified on Mar. 16, 2010, pp. 1-2.
Li et al. "Influence of Lignosulfonates on the Properties of Dimethomorph Water-Didpersible Granules", Bioresources 4(2), 2009, pp. 589-601.
Lauten et al. "New Developments in the Commercial Utlization of Lignosulfonates", Surfactants From Renewable Resources (2010), pp. 269-283.
Akzo Nobel "Morwet D-425 Power", Morwet, Issued May 3, 2011;1(1), p. 1.
Akzo Nobel "New Morwet Naphthalene Sulfonate Condensate Dispersant for SC, WP and WDG Formulations", Sureface Chemistry News, Jul.-Aug. 2010, p. 1.
"Morwet D-390 Powder", Spectrum Chemicals,(2010), pp. 1-4.
Rohm and Haas "Tamol 850 Dispersing Agent, 60230", http://hazard.com/msds/f2/bnk/bnkyt.html, Apr. 26, 1988, pp. 1-2.
Gessner G. Hawley, The Condensed Chemical Dictionary, Van Nostrand Reinhold Company, 1905-QD5.C5 1976, pp. 1-3.
Union Carbide "Ucar Latex 1635",Building Products, 2000, pp. 1-8.
Trading Chem "Castor Oil, Ethoxylated(61791-12-6)", www.tradingchem.com/castor_oil_ethoxylated/61791-12-6.html, Accessed on Jul. 14, 2011, p. 1.
P.J.Mulqueen "Surfactants for Agrochemical Formulation" in "Industrial Applications of Surfactants II", The Royal Society of Chemistry, Dow Chemical Company Limited,Letcombe Laboratory, Letcombe Regis, Wantage, Oxfordshire OX12 9JT, UK, 1990, pp. 1-16.

\* cited by examiner

FERTILIZER-COMPATIBLE COMPOSITION

RELATED APPLICATIONS

This application is a continuation-in-part of U.S. application Ser. No. 11/041,167, filed Jan. 21, 2005 now abandoned.

BACKGROUND OF THE INVENTION

The present invention relates to compositions for use in agricultural and non-agricultural pest control applications, such as control of insects, weeds, and fungi.

Many pesticide formulations are tank-mixed as liquids in the field with many other pesticides, adjuvants, and the like to maximize application efficiency. Many tank mixtures include two or more pesticides and/or fertilizers.

Compatibility of fertilizers with pesticides in tank-mixtures has proved a persistently troublesome problem. For example, chloronicontinyl (CNI) insecticides are known to be effective insecticides in agricultural and non-agricultural pest control, a known problem of this class of insecticides and other pesticides in general is the compatibility with fertilizers, particularly liquid fertilizer compositions. Despite the years of research, there is no general solution to the incompatibility problem, although earlier practitioners have provided several proposed solutions, e.g., U.S. Pat. Nos. 4,464,193, 5,516,747, and 4,071,617.

A major challenge lies in the unpredictability and complex nature of the final tank-mixtures. There are two general types of incompatibility of pesticides and fertilizers: chemical and physical. For example chemical incompatibility of a pesticide and fertilizer occurs when a pesticide is hydrolyzed or subjected to other unwanted chemical reactions. Physical incompatibility occurs most frequently when the tank mixture forms an agglomerate due to, e.g., coagulation, flocculation, gelling, or precipitation of crystals. The mixtures may form hard packed agglomerates or oil globules. Physical incompatibility present difficulties since the malfunctioning tank-mixture plugs conventional spray filters and nozzles.

The problem can be persistent despite the use of compatibility agents which mostly are organic nonionic surfactants. Between the two incompatibility types, the physical incompatibility is the most serious of all, since chemical incompatibility can be generally avoided beforehand. Physical incompatibility is generally overcome by use of surfactants or wetting agents and dispersants. Although there have been pesticide suspension patents of fertilizer compatible compositions as described above, they are found to suffer from one major problem, foaming. This can be a persistent problem during tank mixing with fertilizers, apparently caused by the presence of surfactant combinations. As a result, the foaming problem can lead to inaccurate spray volume of the fertilizer mix.

SUMMARY OF THE INVENTION

The present invention provides a fluid thixotropic composition comprising
(a) an agrochemically active compound;
(b) a metal lignosulfate salt;
(c) a water soluble salt of a strong acid; and
(d) water;
wherein the compound is in the form of solid particles and/or liquid globules of sufficiently small average diameter to be effectively dispersed in the composition and wherein the metal lignosulfate salt and water soluble salt are combined in amounts effective to disperse the particles and/or globules in the water.

DETAILED DESCRIPTION OF THE INVENTION

The agrochemically active compounds used in this invention include insecticides, herbicides, fungicides, and plant growth regulants, as well as their physical mixtures. For chemical classes and applications, as well as specific compounds of each class, see *The Pesticide Manual*, Thirteenth Edition (British Crop Protection Council, Hampshire, UK, 2003), as well as *The e-Pesticide Manual*, Version 3 (British Crop Protection Council, Hampshire, UK, 2003-04)

Preferred agrochemically active compounds are solids that are partially soluble, insoluble, or substantially insoluble in water. Preferably, a suspension concentrate (SC or FS (when referring to seed treatment)) is made of a fine solid dispersion in aqueous medium. The essential technique for making SC or FS involves fine-grinding and dispersing the solid active compound in the formulation aqueous phase by any of the well-known methods for doing so. Generally the technique involves adding a combined mixture of surfactants (e.g., wetting agents) and dispersant (e.g., known nonionic surfactants and water soluble polymers) along with the active solid to the medium while mechanically reducing the particle size of the solids. In addition, when the agrochemically active compounds are physically liquid in form (i.e., with a melting point below about 20° C.), the preferred formulation type is either an emulsion (EW) or suspoemulsion (SE) for solid/liquid mixture with the liquid oil phase dispersed in the aqueous medium by this technology. Mostly the liquid active is the oil phase or in the oil phase which may also contain a hydrophobic solvent. Furthermore, the liquid active compound is mechanically dispersed and emulsified in the aqueous medium with the aid of a surfactant of low HLB values (2 to 12). The surfactant can be of dispersing type (dispersing agent or dispersant) or wetting type (wetting agent) or functionally both dispersing and wetting and can also be ionic or nonionic and polymeric in structure. One noted characteristic of the surfactants is their ability to lower the surface tension of the aqueous medium of SC or FS or SE formulations. On the other hand, there is also a category of ionic water soluble polymers that function only as a dispersing agent with no significant surface activity (e.g., M. J. Rosen, *Surfactants and Interfacial Phenomena* (John Wiley & Sons, 1978), pages 8-9). Examples of this type of surfactant are lignin sulfonates as discussed in detail below. For an SE formulation, the mixing of the EC portion with the SC portion is carried out after each portion is prepared separately beforehand.

The metal lignosulfate salt may be any salt of a lignosulfonic acid which is effective to disperse the insecticide. Typical metal counterions include sodium, potassium, lithium, and calcium. Two or more lignosulfate salts may be combined in effective amounts to provide an adequate dispersant. For example, sodium lignosulfate and calcium lignosulfate may be combined in effective amounts.

Should it be necessary, an ammonium lignosulfate salt may be used, e.g., a tetraalkyl ammonium or aryltrialkylammonium counterion may be used. Examples of these types of dispersants include tetrabutyl ammonium lignosulfate and phenyltrimethylammonium lignosulfate.

The lignosulfate anion moiety of the metal lignosulfate salt is generally a product of the sulfonation of lignin. The anion may comprise polymeric molecules of weight-average molecular weight from about 2000 to 100000 g/mol (Daltons). A preferred molecular weight range is between 1000 and 80,000, more preferably from 2000 to 60000 with carbon to sulfur ratio between 9:1 to 55:1. A preferred molecular weight range is from 20000 to 30000, and a number average molecular weight of from about 1000 to about 10000 g/mol. More preferably, the molecular weight of the metal lignosulfate salt is from 2000 g/mol to about 8000 g/mol. Examples of these types of lignosulfonic acid salts include Borresperse® NA sodium lignosulfonate dispersant, Borresperse® CA calcium lignosulfate dispersant, Ultrazine® NA sodium lignosulfonate dispersant and Ultrazine® CA calcium lignosulfate dispersant. All of these dispersants are available from the Borregaard® Lignotech Company (Internet: http//:www.lignotech.com) at Borregaard P.O. Box 162 NO-1701 Sarpsborg, Norway.

The metal content of the metal lignosulfate is generally from 0.2% to 15% by weight if sodium or from 0.1 to 0.9% if calcium. The amount of sulfonation of the lignin polymer is generally from 2 to 10% by weight. The degree of sulfonation is generally from 0.5% to 3%.

Generally, one or more of the following types of lignin-based dispersants may be used: mono-calcium salt of polymerized aryl alkylsulfonic acids, (lignosulfonate calcium salt); sodium salt of kraft lignin polymer optionally mixed with a modified sulfite lignin; ammonium lignosulfonates; lignin, alkali, and reaction product with sodium bisulfite and formaldehyde.

Metal lignosulfate salts are materials that may be prepared from the waste liquor of sulfite pulping. Then they are further oxidized, or desulfonated. Generally, lignin sulfonates are water soluble polymers carrying ionic charge along the backbone chain, including ammonium, sodium, calcium and magnesium ions.

The metal lignosulfate salt of the invention is used in an amount effective to provide adsorption of the metal lignosulfate salt on the surfaces of the pesticide particles or globules to impart a negative charge to the particle or globule. The resulting electrostatic repulsions between particles or globules then prevent heavy flocculation and aggregation. The effective amount of the metal lignosulfate salts is generally from about 0.5% to about 25%, preferably from about 2 to about 10%.

Examples of useful metal lignosulfate salts include those in Table 1.

TABLE 1

| Chemical Characterization | Chem. Abst. Number | Trade Name |
|---|---|---|
| Mono-calcium salt of polymerized aryl alkylsulfonic acids or lignosulfonic acid, calcium salt | 8061-52-7 | |
| Naphthalene sulfonic acid formaldehyde condensate, ammonium and sodium salt | 83453-42-3 | Krafsperse, polyfon, Reax, mixtures |
| Sulfonated alkyl naphthalene Condensates, naphthalenesulfonic acid-formaldehyde, sodium salt, NaNS-F, naphthalene sulfonate calcium salt | 9084-06-4 | Supragil MNS/90, Supragil WP, Morwet D425 |
| Sulfonated kraft lignin and naphthalene sulfonate mixture | | Krafsperse |
| Sodium salt of kraft lignin polymer/ Modified sulfite lignin | 8061-51-6 | Polyfon |
| Sodium salt of sulfonated modified kraft lignin | 105859-97-0 | Reax series |
| Lignin, alkali, reaction product with disodium sulfite and formaldehyde | 105859-97-0 | |
| Lignosulfonic acid, sodium salt, sulfomethylated | 68512-34-5 | |
| Ethoxylated sodium salt of sulfonated kraft lignin | 68611-14-3 | |
| Lignin, alkali, reaction product with sodium bisulfite and formaldehyde | 68512-35-6 | |
| Kraft lignin | 8068-05-1 | |
| Ammonium lignosulfonate etc. | 8061-53-8 | |
| Lignin, alkali, oxidized, sodium salt | 68201-23-0 | |
| Ligninderivat | 105859-97-0 | |
| Lignosulfonic acid | 8062-15-5 | |
| Lignosulfonic acid, magnesium salt | 8061-54-9 | |
| Lignosulfonic acid, potassium salt | 37314-65-1 | |
| Lignin Solids | 9005-53-2 | |

The salts in this invention generally are water soluble alkali metal, alkaline earth metal or ammonium salts of a strong acid. Salts include aluminum chloride, copper chloride, iron(II) chloride, iron (III) chloride, lithium chloride, sodium chloride, potassium chloride, ammonium chloride, magnesium chloride, calcium chloride, zinc chloride, aluminum nitrate, ammonium nitrate, copper nitrate, iron(II) nitrate, iron(III) nitrate, lithium nitrate, sodium nitrate, potassium nitrate, magnesium nitrate, calcium nitrate, aluminum sulfate, copper sulfate, iron(II) sulfate, lithium sulfate, sodium sulfate, potassium sulfate, potassium hydrogen sulfate, ammonium sulfate, magnesium sulfate, sodium monhydrogen phosphate, potassium monhydrogen phosphate, potassium phosphate, ammonium mono-hydrogen phosphate, sodium dihydrogen phosphate, potassium dihydrogen phosphate, ammonium dihydrogen phosphate, zinc sulfate, lithium trifluoroacetate, sodium trifluoroacetate, and potassium trifluoroacetate. The composition also includes mixtures of two or more.

Generally the salt and the lignosulfate salt are admixed to provide an optimum mixture. Generally the metal lignosulfate salt and the water soluble salt are present in a ratio of from about 2:1 to about 1:20, preferably from 1:1 to 1:10.

Generally the insecticide and metal lignosulfate salt are present at a ratio of from about 60:1 to about 1:10, preferably from about 20:1 to about 1:5, most preferably from about 20:1 to 1:1.

The fluid composition of the invention may further comprise one or more of the following features:
(e) a diluent;
(f) a surfactant;
(g) a lubricant;
(h) an adjuvant;
(i) an antifoaming agent;
(j) a biocide; and
(k) a colorant.

The composition of the invention is generally a controlled flocculation. In general, the composition is substantially a thixotropic suspension. If the average diameter of the particles or globules of the compound is from 1 nm to 5 microns (preferably 1 to 5 microns), then the suspension is colloidal; if the average diameter of the particles or globules is from 5 microns to 100 microns (preferably greater than 5 microns), then the suspension is a coarse suspension. Ideally the particles or globules are of average diameter of from about 1 micron to about 10 microns, preferably 2 to 4 microns.

In a preferred embodiment, the fluid composition of the present invention is either substantially free of a surfactant or contains mostly a non-surface active dispersant, especially when solid active ingredients with melting points above 20° C. are involved. The resultant formulation type is a suspension concentrate.

However, the composition can also employ mixtures of lignin sulfonates with water soluble anionic and/or nonionic (preferably anionic) surfactants described below. Moreover, it is also possible for mixing the water soluble synthetic polymers of the alkali metal salts of homo- and co-polyacrylates with acrylic and methacrylates and the alkali metal salts of polystyrene sulfonate with other organic sulfonates and water soluble anionic and/or nonionic (preferably anionic) surfactants.

The organic sulfonates in particular include ammonium, sodium, and calcium salts of alkyl naphthalene sulfonate; and ammonium and sodium salts of naphthalene formaldehyde sulfonate (CAS 83453-42-3); sodium bis (1-methylethyl) naphthalene sulfonate (CAS 1322-93-6); sodium naphthalene formaldehyde sulfonate (CAS 9084-06-4); sodium 2-naphthalene formaldehyde sulfonate (CAS 29321-75-3); sodium isethionate; sodium taurates; petroleum sulfonates, paraffin sulfonates, α-olefin sufonates and sulfosuccinates, sulfated alchohols and sulfated polyoxyethylenated alcohols, sulfated castor oil and other sulfated triglyceride oils, and sodium alkylbenzene sulfonates (benzene, toluene, xylene, and cumene sulfonates) (e.g., M. J. Rosen, *Surfactants and Interfacial Phenomena* (John Wiley & Sons, 1978), pages 7-8) and sodium salt of the straight chain alkylbenzenesulfonates: (expressed in LAS/CAS code/salt): ($C_{10-13}$)alkyl-CAS 68411-30-3 (sodium salt); ($C_{10-16}$)alkyl-CAS 68584-22-5, CAS 68584-23-6 (calcium salt) CAS 68584-26-9 (magnesium salt) CAS 68584-27-0 (potassium salt); mono($C_{6-12}$)alkyl-CAS 68608-87-7 (sodium salt); mono($C_{7-17}$)alkyl-CAS 68953-91-3 (calcium salt) CAS 68953-94-6 (potassium salt); mono($C_{9-12}$) alkyl-CAS 68953-95-7 (sodium salt); mono($C_{10-16}$)alkyl-CAS 68910-31-6 (ammonium salt) CAS 68081-81-2 (sodium salt); and mono($C_{12-18}$)alkyl-CAS 68648-97-5 (potassium salt).

Surfactants can be of the emulsifying or wetting type and can be ionic or nonionic. Possible surfactants include alkali metal, alkaline earth metal and ammonium salts of alkylsulfonic, phenylsulfonic or naphthalenesulfonic acids; polycondensates of ethylene oxide with fatty alcohols or fatty acids or fatty amines or substituted phenols (particularly alkylphenols or arylphenols); ester-salts of sulfosuccinic acids; taurine derivatives, such as alkyl taurates; phosphoric esters; or esters of alcohols or polyoxyethylated phenols. If a surfactant is used, it is preferential to use a nonionic surfactant. However, the nonionic surfactant is used in an effective amount to improve the composition but in an amount to minimize foaming of the composition upon physical mixing or dilution into water. Generally the amount of any nonionic surfactant is from 0.1 to 1% of the composition, preferably from 0.1 to 0.5% by weight of the composition. One critical criterion is that both the anionic and the nonionic surfactant must meet the requirement that they dissolve or be at least substantially miscible in the aqueous medium. Preferably the HLB of the nonionic surfactant is from about 10 to about 20.

A general description of surfactants that might be used in the present invention include nonionic surfactants such as $C_8$ to $C_{18}$ alcohol alkoxylates, both linear and branched chain ethoxylates with 2 to 22 (preferably 2 to 10) EO units and with an HLB range from about 4 to 16 (preferably 2 to 12); alkyl phenol ethoxylates, mono- and di-nonyl and octyl phenol with 2 to 150 (preferably 2 to 40) EO units, HLB range from about 4 to 19 (preferably 4 to 12); fatty amine alkoxylates, e.g., tallow, oleyl, stearyl and cocoamine alkoxylates with 2 to 50 EO (preferably 2 to 20) units and HLB range from about 4 to 18 (preferably 4 to 12); alkanolamides; triglyceride alkoxylates, such as castor, rapeseed, soybean and colza oil ethoxylates with 5 to 54 (preferably 5 to 20) EO units and HLB range from about 4 to 15 (preferably 4 to 12); sorbitan ester ethoxylates with 20 to 30 EO units, HLB range from about 10 to 16 (preferably 10 to 12); ethylene oxide/propylene oxide copolymers including alkoxylated rapeseed oil with ethylene oxide and propylene oxide chains; and with an HLB range from about 1 to 18 (preferably 1 to 18); alkyl polyglycosides; fatty acid ethoxylates; fatty acid polyethylene glycols; fatty alcohol ethoxylates; di- and tristyrylphenol ethoxylates; glycerol esters; and polyol ethoxylate esters.

Anionic surfactants that may be used in the present invention include sulfates, fatty alcohol ether sulfates, fatty acid sulfates; sulfonates, alkylbenzenesulfonates, alkyl naphthalene sulfonates, alkylaryl sulfonates, olefin sulfonates, alkylphenol ethoxylate sulfates; phosphates, such as phosphates of fatty alcohol ethoxylate, phosphates of alkylphenol ethoxylate having 4 to 12 EO units; alkyl sulfosuccinates; carboxylates, alkylphenol ethoxylate carboxylates.

For SE formulation types, both anionic or nonionic surfactants or mixtures thereof can be used to disperse the hydrophobic liquid phase (the EC oil). Typically, a mixture of anionic and nonionic surfactants, as well as oil soluble nonionic-polymers, is used to disperse the oil phase.

Suitable oil soluble anionic surfactants include n- and iso-$C_{12}$-alkylbenzene calcium sulfonate salts and other oil soluble alkylbenzene sulfonate salts. Suitable soluble nonionic surfactants include nonylphenol ethoxylates (HLB of about 2 to 12), octylphenol ethoxylates (HLB of about 2 to 12), tributylphenol ethoxylates (HLB of about 2 to 12), alkoxylates (EO/PO) (HLB of about 2 to 12), tristyrylphenol ethoxylates (HLB of about 2 to 12), fatty alcohol ethoxylates (such as $C_9$-$C_{11}$, $C_{12}$-$C_{14}$ fatty alcohol polyglycol ether, $C_{11}$, $C_{12}$-$C_{15}$, $C_{14}$-$C_{16}$, and $C_{16}$-$C_{18}$ fatty oxo alcohol polyglycol ether, and oleyl alcohol poly glycol ether, HLB of about 2 to 12), stearyl alcohol ethoxylates, isotridecyl alcohol polyglycol ether (HLB of about 2 to 12), oleyl cetyl alcohol ethoxylates, isodecyl and tridecyl alcohol ethoxylates, sorbitan ethoxylates, sorbitan monooleate ethoxylates, sorbitan trioleate ethoxylates, sorbitan tristearate ethoxylates, sorbitan monolaurate ethoxylates, sorbitol oleate ethoxylates, fatty amine ethoxylates (coco amine and tallow amine and stearyl amine ethoxylates), and glycerol oleate ethoxylate.

Polymeric dispersants for dispersing the oil phase in the present invention include polyethylene glycol alkyds (e.g., Atlox 4914), A-B-A type block copolymers of 12 isohydroxystearic acid), polyethyleneglycols (e.g., Atlox 4912), and alkylated vinylpyrrolidone polymers (e.g., Agrimer AL 22, 25, and 30).

Furthermore, to disperse the suspension portion of SE formulations, only lignin sulfonates and optional organic sulfonates are required to disperse the active solids. Moreover, after combining the SC and EC portions, additional anionic and nonionic surfactants may be used in the aqueous phase to further improve the SE formulation stability. For anionic surfactants, this may include phenyl sulfonates, alkylbenzene sulfonates, n- and iso-$C_{12}$-alkylbenzene sulfonates, sodium or triethanolamine salt, sodium octylphenol polyglycol ether sulfate, sodium nonylphenol polyglycol ether sulfate, sodium fatty alcohol polyglycol ether sulfate, sodium lauryl ether sulfate, phosphated salts of tristyrylphenol ethoxylates, phosphate ester of EO/PO block copolymer, alkylphenol ethoxylate phosphates, phosphated alkyl polyglycol ether ethoxylate ester, fatty acid tauride sodium salt, and ether sulfates. For nonionic surfactants, this may include di- and tristrylphenol ethoxylates, castor oil ethoxylates, rapeseed oil alkoxylates, soybean oil ethoxylates, and isotridecyl alcohol ethoxylate and alkyl ($C_8$-$C_{10}$) polyglycosides. The average HLB of the nonionics for the aqueous phase is about 11 to 20. it is also possible to use EO/PO block copolymers (Pluronics®), and $C_{12}$-$C_{14}$ alcohol EO/PO block copolymers. The anionic or nonionic surfactant is used in an effective amount to improve the composition but in an amount to minimize foaming of the composition upon physical mixing or dilution into water.

Information about the surfactants can be obtained from "McCutcheon's Emulsifiers & Detergents," McCutcheon Division, McCutcheon Publishing Co., 175 Rock Road, Glen Rock, N.J. 07452.

By the term diluent is meant a liquid which decreases the concentration of the compound of formula (I) in the fluid. Preferred diluents also are added in sufficient amounts to increase the viscosity of the fluid and provide a resulting fluid with thixotropic properties. The diluent may also function as an antifreeze. Examples of preferred diluents include the poly-hydroxylated alkanes, e.g., ethylene glycol, propylene glycol (otherwise known as glycerin, or 1,2,3-propanetriol), tetramethylene glyol, penta-methylene glycol, triethylene glycol, diethylene glycol, glycerin, hexa-methylene glycol and a polyethylene glycol. Generally, diluents have a density of from 1 to 4 g/mL at standard temperature and standard pressure (25° C. and 760 mm Hg respectively) and a viscosity of from 2000 to 4000 cp (centipoise) as measured by an rotating plate Ostwald viscosimeter at standard temperature and pressure.

It is possible to add solvents to the hydrophobic oil phase in se formulations to facilitate emulsion dilution, crystallization control or bioefficacy improvement. Suitable solvents include benzyl alcohol, cyclohexanol, 1-decanol, 1-heptanol, 1-hexanol, isodecyl alcohol, 1-octanol, tridecyl alcohol, acetophenone, benzophenone, cyclohexanone, isophorone, acetyl tributyl citrate, oxo-decyl acetate, oxo-heptyl acetate, acetate esters ($C_6$-$C_{13}$) from highly branched oxo alcohols, methyl caprylate, methyl caprate, alkoxyalkyl lactam, n-2-ethylhexylpyrrolidone, octylpyrrolidone, butylene carbonate, dodecylpyrrolidone, propylene carbonate, canola oil, corn oil, cotton seed oil, oleic acid, paraffin oil, safflower oil, soybean oil, aliphatic solvents ($C_{16}$-$C_{25}$), isoparaffins, normal paraffins ($C_{10}$-$C_{20}$), dearomatic aliphatics, $C_9$-$C_{11}$, isoparaffinic solvent, $C_{11}$-$C_{12}$ isoparaffinic solvent, $C_{12}$-$C_{13}$ isoparaffinic solvent, $C_{12}$-$C_{16}$ isoparaffinic solvent, $C_{14}$-$C_{18}$ isoparaffinic solvent, $C_{15}$-$C_{19}$ isoparaffinic solvent, $C_{10}$ cycloolefin, mineral spirit, aromatic solvents, Exxon Aromatic 100, Exxon Aromatic 150, Exxon Aromatic 200, $C_9$-$C_{12}$ alkylbenzenes, $C_{10}$-$C_{14}$ aromatics, cyclohexane, dearomatized aliphatic solvent, ethyl-benzene, hydrogenated petroleum oils, highly refined petroleum oil, normal paraffins, naphthalene depleted aromatic solvents, petroleum distillate, solvent naphtha, xylene, and mixtures thereof.

Lubricants used in the present invention which enhance mechanical shearing of the composition include silica prepared by precipitating water glass (sodium silicate) with sulfuric acid, which is then dried and sold as a fine powder. The silica powder functions as a viscosity builder yet providing rheology control and aid in suspension by preventing a settling effect. Use of such a lubricant to form an effective thixotrope allows the formulation particles or globules to self assemble into a mechanically shearable composition.

Another lubricant is fumed alumina. Fumed alumina is produced by the hydrolysis of aluminum trichloride in a hydrogen-oxygen flame. The combustions process creates aluminum oxide molecules which condense to form primary particles which sinter together to form aggregates. These aggregates have a chain-like structure and an average diameter of 0.1 and 0.2 microns.

Fumed alumina in this invention, like the precipitated silica, has small particle size in the submicron range (for primary particle size of 20 nm and aggregate size of 150 nm) down to nanometer particle size with B.E.T. surface area of 55 $m^2$/g. It also provides rheology control and lubrication for the suspension concentrate.

Clays may also be optionally used in the present composition. Such clays include kaolinite, dickite, and nacrite, with the general formula of $Al_2Si_2O_5(OH)_4$; pyrophylite, talc, vermiculite, sauconite, saponte, nontronite, and montmorillonite with the general chemical formula (Ca, Na, H) (Al, Mg, Fe, Zn)$_2$ (Si, Al)$_4O_{10}$(OH)$_2$.x$H_2O$; attapulgite with the general chemical formula $Mg_5Si_8O_{20}$(HO)$_2$(OH$_2$)$_4$.4$H_2O$; and illite with the general formula (K, H) Al2(Si, Al)$_4O_{10}$ (OH)$_2$.x$H_2O$.

Adjuvants as used herein are organic hydrophobic hydrocarbons that are derived from either plant or petroleum sources and improve the penetration and bioefficacy of pesticides, insecticides, herbicides, fungicides, and plant growth regulants. The mechanism of the bioefficacy improvement involves spreading, penetration, activation, and adsorption. Suitable adjuvants include methylated and ethylated vegetable oils; methylated, ethylated, and butylated seed oils; and fatty acids such as caproic acid, caprylic acid, erucic acid, lauric acid, linolenic acid, linoleic acid, myristic acid, oleic acid, palmitic acid, stearic acid, and mixtures thereof. Also included are vegetable oils such as canola, corn, cotton, palm, rapeseed, safflower, soybean, and sunflower oils, and mixtures thereof. Furthermore, paraffin ($C_{16}$-$C_{30}$), naphthalene, aromatic-based petroleum oils and mixtures thereof, and crop oil (petroleum based) concentrate containing some nonionic surfactant (HLB of about 2 to 12) or the oil soluble polymers described above. The nonionic surfactants used in this invention not only emulsify the oil phase but also may act as adjuvants that promote the bioefficacy of the pesticides, insecticides, herbicides, fungicides, and plant growth regulants. All the above oils can also be further admixed with organo-silicone surfactants.

Additional components that can be used in the compositions of the invention include known antifoaming agents, biocides, and colorants (which can be either dyes or pigments, depending on the application).

Although formulations in this invention generally have low foaming tendency without the need for defoamers or antifoams, small amounts of amount of defoamer or antifoam compounds may be included to further reduce the foam formation when handling or transporting the formulations. Defoamers and antifoams in emulsion form that are compatible with the SC and SE formulation of this invention include both silicone and non-silicone based antifoams, such as polydimethyl siloxanes, organo-modified siloxanes, alkyl-, aryl-, and aralkyl-modified siloxanes, emulsions of polydimethyl siloxanes, mineral oil based defoamers, petroleum based defoamers, silicone oil based defoamers, Star®) polymers, and fatty acid soaps. The effective range for these defoamers and antifoams is about 0.0005 to 3%, preferably from 0.005 to 1%.

Suitable biocides (particularly bactericides) include 1, 2-benziso-thiazolin-3-one (e.g., trade name, Proxel GXL), 5-chloro-2-methyl-3(2H)-isothiazolone (e.g., trade name, Kathon), o-phenylphenol, sodium o-phenylphenate, cis-1-(chloroallyl)-3,5,7-triaza-1-azoniaadamantane chloride, 7-ethyl bicyclooxazolidine, 2,2-dibromo-3-nitrilopropionamide, bronopol, glutaraldehyde, copper hydroxide, cresol, dichlorophen, dipyrithione, dodidin, fenaminosulf, formaldehyde, hydrargaphen, 8-hydroxyquinoline sulfate, kasugamycin, nitrapyrin, octhilinone, oxolinic acid, oxytetracycline, probenazole, streptomycin, tecloftalam, thimerosal, polyquaternary ammonium chloride, and alkylbenzyl dimethyl ammonium chloride. The effective amount in the formulations is from about 0.1 to 3%, preferably from 0.3 to 1.5%.

Suitable colorants include pigments and dyes known in the art. Both natural and synthetic inorganic pigments can be used in the SC and SE formulation types of this invention without stability problems. Suitable natural inorganic pigments include natural oxides, hydroxides, sulfides, sulfates, silicates, and carbonates of many mineral elements (e.g., iron, magnesium, potassium, aluminum, and copper) as well as mixtures thereof. Red earths, yellow earths, green earths, lapis lazuli, azurite, malachite, other traditional earth colors, and mixtures thereof have been the main sources of natural inorganic pigments. Suitable synthetic inorganic pigments include ferric ammonium ferrocyanide, iron oxide, iron oxide yellow, iron oxide brown, iron oxide orange, iron oxide red, iron oxide black, iron blue, cobalt green, cobalt blue, zinc oxide, zinc sulfide, chrome titanium oxide (Pigment White 6), chromium oxide green (anhydrous), hydrated chrome oxide green, Prussian green, cyanine blue, manganese blue, manganese violet, titanium dioxide, and mixtures thereof. Furthermore, synthetic inorganic pigments made of oxide-coated micas, which may be either titanium dioxide or iron oxide coated micas, can also be used in this invention. Organic pigments in this invention include (using Colour Index names) Pigment Blue 1, Pigment Blue 15, Pigment Blue 15:1, Pigment Blue 15:3, Pigment Blue 15:4, Pigment Blue 61, Pigment Blue 62, Pigment Green 7, Pigment Green 36, Pigment Orange 5, Pigment Orange 13, Pigment Orange 16, Pigment Orange 34, Pigment Orange 36, Pigment Orange 46, Pigment Red 2, Pigment Red 3, Pigment Red 4, Pigment Red 12, Pigment Red 17, Pigment Red 22, Pigment Red 23, Pigment Red 38, Pigment Red 48:1, Pigment Red 48:2, Pigment Red 48:3, Pigment Red 48:4, Pigment Red 49:1, Pigment Red 49:2, Pigment Red 52:1, Pigment Red 53:1, Pigment Red 57, Pigment Red 57:1, Pigment Red 60:1, Pigment Red 63:1, Pigment Red 81, Pigment Red 81:3, Pigment Red 90, Pigment Red 112, Pigment Red 169, Pigment Red 170, Pigment Red 202, Pigment Red 210, Pigment Violet 1, Pigment Violet 3, Pigment Violet 19, Pigment Violet 23, Pigment Violet 27, Pigment Violet 29, Pigment Yellow 1, Pigment Yellow 3, Pigment Yellow 12, Pigment Yellow 13, Pigment Yellow 14, Pigment Yellow 17, Pigment Yellow 62, Pigment Yellow 65, Pigment Yellow 73, Pigment Yellow 74, Pigment Yellow 75, Pigment Yellow 83, Pigment Yellow 111, Pigment Yellow 126, Pigment Yellow 168, Pigment Yellow 184, and mixtures thereof. The inorganic and organic pigment can be either a dry powder, slurry, or suspension and can be high solids pigments. The solids content of the pigments can range from about 20 to 70%, the optimum range being from 30 to 65%. Either the solids or the slurry can be post-added and stirred in easily with agitation after the SC or SE formulation is made. The amount of the pigment in the formulation is from about 0.1 to 6%, preferably from 0.1 to 2%.

Water-soluble dyes can be used in the SC and SE formulation types of this invention without stability problems. Suitable dyes include Acid Black 172, Acid Black 194, Acid Black 210, Acid Blue 1, Acid Blue 7, Acid Blue 9, Acid Blue 93, Acid Blue 93:1, Acid Green 16, Acid Green 25, Acid Orange 10, Acid Red 14, Acid Red 17, Acid Red 18, Acid Red 52, Acid Violet 17, Acid Violet 49, Acid Yellow 23, Acid Yellow 36, Basic Blue 26, Basic Blue 3, Basic Blue 41, Basic Blue 54, Basic Blue 7, Basic Blue 9, Basic Brown 4, Basic Brown1, Basic Green 1, Basic Green 4, Basic Orange 1, Basic Orange 2, Basic Orange 21, Basic Red 14, Basic Red 15, Basic Red 18, Basic Red 22, Basic Red 46, Basic Red 49, Basic Violet 1, Basic Violet 10, Basic Violet 14, Basic Violet 16, Basic Violet 2, Basic Violet 3, Basic Violet 4, Basic Yellow 11, Basic Yellow 13, Basic Yellow 2, Basic Yellow 21, Basic Yellow 28, Basic Yellow, 9, Basic Yellow 37, Basic Yellow 40, D&C Green 5, D&C Green 6, D&C Green 8, D&C Orange 4, D&C Orange 5, D&C Red 17, D&C Red 21, D&C Red 22, D&C Red 27, D&C Red 28, D&C Red 30, D&C Red 33, D&C Red 34, D&C Red 36, D&C Red 6, D&C Red 7, D&C Red 8, D&C Violet 2, D&C Yellow 10, D&C Yellow 11, D&C Yellow 7, D&C Yellow 8, FD&C Blue 1, FD&C Blue 2, FD&C Green 3, FD&C Red 3, FD&C Red 4, FD&C Red 40, FD&C Yellow 5 (tartrazine), FD&C Yellow 6, and mixtures thereof. The dyes can be post-added and stirred in easily with agitation after the SC or SE formulation is made. The amount of the dye in the formulation is from about 0.01 to 5%, the optimum range being from 0.02 to 2%.

Fertilizers that are compatible with the composition of the present invention are generally liquid fertilizer compositions for any available use. Such fertilizers are generally measured by a nitrogen-phosphorous-potassium index providing the amounts of each ingredient as a weight-weight percentage of each major component. Nitrogen content is generally from 1 to 40%; phosphorous content is from 0 to 55% and potassium content is from 0 to 15%. Generally the liquid fertilizers are formulated as an aqueous composition. Such fertilizers are known to those of ordinary skill in the art.

The composition of the invention is also substantially compatible with micronutrient compositions which contain such elements as boron, cobalt, copper, iron, magnesium, molybdenum, potassium, sodium, sulfur and zinc ions.

Suitable agrochemically active compounds used according to this invention include insecticides. As used herein, the term "insecticide" broadly refers to compounds or compositions that are used as acaricides, insecticides, insecticide synergists, ixodicides, nematicides, and molluscicides. Chemical classes of insecticides include 2-dimethylaminopropane-1,3-dithiol, 2-dimethylaminopropane-1,3-dithiol analogs, amidines, arylpyrroles, avermectin, benzoylureas, carbamates, carbamoyl-triazoles, cyclodienes, diacylhydrazines, dinitrophenols, fiprole, METI, neonicotinoids, non-ester pyrethroids, organochlorines, organophosphates, oxadiazines, oximes, carbamates, pyrethroids, and spinosyns. Suitable insecticides include 1,1-bis(4-chlorophenyl)-2-ethoxyethanol, 1,1-dichloro-1-nitroethane, 1,1-dichloro-2,2-bis(4-ethylphenyl)ethane, 1,2-dichloropropane with 1,3-dichloropropene, 1-bromo-2-chloroethane, 2-(1,3-dithiolan-2-yl)phenyl dimethylcarbamate, 2-(2-butoxyethoxy)ethyl thiocyanate, 2-(4,5-dimethyl-1,3-dioxolan-2-yl)phenyl methylcarbamate, 2-(4-chloro-3,5-xylyloxy)ethanol, 2,2,2-trichloro-1-(3,4-dichlorophenyl)ethyl acetate, 2,2-dichlorovinyl 2-ethylsulfinylethyl methyl phosphate, 2,4-dichlorophenyl benzenesulfonate, 2-chlorovinyl diethyl phosphate, 2-isovalerylindan-1,3-dione, 2-methyl(prop-2-ynyl)aminophenyl methylcarbamate, 2-thiocyanatoethyl laurate, 3-bromo-1-chloroprop-1-ene, 3-methyl-1-phenylpyrazol-5-yl dimethylcarbamate, 4-chlorophenyl phenyl sulfone, 4-methyl(prop-2-ynyl)amino-3,5-xylyl methylcarbamate, 4-methylnonan-5-ol with 4-methylnonan-5-one, 5,5-dimethyl-3-oxocyclohex-1-enyl dimethylcarbamate, 6-methylhept-2-en-4-ol, abamectin, acephate acequinocyl, acrinathrin, alanycarb, aldicarb, aldoxycarb, aldrin, allethrin [(1R)-isomers], allyxycarb, alpha-cypermethrin, amidithion, amidothioate, aminocarb, amiton; amiton hydrogen oxalate, amitraz, anabasine, aramite, athidathion, azadirachtin, azamethiphos, azinphos-eth yl, azinphos-methyl, azocyclotin, azothoate, barium polysulfide, Bayer 22/190, Bayer 22408, bendiocarb, benfuracarb, bensultap, benzoximate, beta-cyfluthrin, beta-cypermethrin, bifenazate, bifenthrin, binapacryl, biopermethrin, bis(2-chloroethyl) ether, bistrifluron, bromfenvinfos, bromocyclen, bromophos, bromophos-ethyl, bromopropylate, bufencarb, buprofezin, butacarb, butathiofos, butocarboxim, butonate, butoxycarboxim, cadusafos, calcium polysulfide, camphechlor, carbanolate, carbaryl, carbofuran, carbophenothion, carbosulfan, cartap hydrochloride, CGA 50 439, chinomethionat, chlorbenside, chlorbicyclen, chlordane, chlordecone, chlordimefo rm; chlordimeform hydrochloride, chlorethoxyfos, chlorfenapyr, chlorfenethol, chlorfenson, chlorfensulphide, chlorfluazuron, chlormephos, chloro-benzilate, chloromebuform, chloropropylate, chlorphoxim, chlorprazophos, chlorpyrifos, chlorpyrifos-methyl, chlorthiophos, chromafenozide, cloetho-carb, clofentezine, clothianidin, codlemone, coumaphos, coumithoate, crotoxyphos, crufomate, cryolite, CS 708, cyanofenphos, cyanophos, cyanthoate, cycloprothrin, cyfluthrin, cyhalothrin, cyhexatin, cypermethrin, cyphenothrin [(1R)-trans-isomers], cyromazine, DAEP, dazomet, DCPM, DDT, decarbofuran, deltamethrin, demephion; demephion-O; demephion-S, demeton; demeton-O; demeton-S, demeton-S-methyl, demeton-S-methylsulphon, diafenthiuron, dialifos, diazinon, dicapthon, dichlorvos, dicofol, dicrotophos, dicyclanil, dieldrin, dienochlor, diethyl 5-methyl-pyrazol-3-yl phosphate, diflubenzuron, dimefox, dimethoate, dimethrin, dimethylvinphos, dimetilan, dinex; dinex-diclexine, dinobuton, dinocap, dinocton, dinopenton, dinoprop, dinosulfon, dinotefuran, dinoterbon, dioxabenzofos, dioxacarb, dioxathion, diphenyl sulfone, disulfoton, dithicrofos, DNOC, dodec-8-enyl acetate, dofenapyn, DSP, EI 1642, emam ectin benzoate, EMPC, empenthrin [(EZ)-(1R)-isomers], endosulfan, endothion, endrin, ENT 8184, EPBP, EPN, esfenvalerate, ethio-fencarb, ethion, ethiprole, ethoate-methyl, ethoprophos, etofenprox, etoxazole, etrimfos, famphur, fenazaflor, fenazaquin, fenbutatin oxide, fenchlorphos, fenethacarb, fenfluthrin, fenitrothion, fenobucarb, fenothiocarb, fenoxacrim, fenoxycarb, fenpirithrin, fenpropathrin, fenpyroximate, fenson, fensulfothion, fenthion, fentrifanil, fenvalerate, fipronil, flonicamid, fluacrypyrim, flubenzimine, flucofuron, flucycloxuron, flucythrinate, fluenetil, flufenoxuron, flufenprox, flumethrin, fluorbenside, fluvalinate, FMC 1137, fonofos, formetanate, formothion, formparanate, fosmethilan, fospirate, fosthiazate, fosthietan, furathiocarb, furethrin, gamma-cyhalothrin, gamma-HCH, glyodin, GY-81, halfenprox, halofenozide, heptachlor, heptenophos, hexadecyl cyclopropanecarboxylate, hexaflumuron, hexythiazox, hydramethylnon, hydroprene, hyquincarb, imidacloprid, imiprothrin, indoxacarb, iprobenfos, IPSP, isazofos, isobenzan, isodrin, isofenphos, isolane, isoprocarb, isopropyl O-(methoxyaminothio-phosphoryl)salicylate, isothioate, isoxathion, jodfenphos, kelevan, kinoprene, lambda-c yhalothrin, leptophos, lirimfos, lufenuron, lythidathion, m-cumenyl methylcarbamate, malathion, malonoben, mazidox, MB-599, mecarbam, mecarphon, menazon, mephosfolan, mercurous chloride, mesulfenfos, metam, methacrifos, methamidophos, methanesulfonyl fluoride, methidathion, methiocarb, methocrotophos, methomyl, methoprene, methoquin-butyl, methothrin, methoxychlor, methoxyfenozide, methyl isothiocyanate, metolcarb, metoxadiazone, mevinphos, mexacarbate, milbemectin, mipafox, mirex, MNFA, monocrotophos, morphothion, naled, naphthalene, nicotine, nifluridide, nitenpyram, nithiazine, nitrilacarb; nitrilacarb 1:1 zinc chloride complex, nornicotine, novaluron, noviflumuron, O,O,O'-tetrapropyl dithiopyrophosphate, O,O-diethyl O-4-methyl-2-oxo-2H-chromen-7-yl phosphorothioate, O,O-diethyl O-6-methyl-2-propylpyrimidin-4-yl phosphorothioate, O-2,5-dichloro-4-iodophenyl O-ethyl ethylphosphonothioate, oleic acid (fatty acids), omethoate, oxabetrinil, oxamyl, oxydemeton-methyl, oxydeprofos, oxydisulfoton, parathion, parathion-methyl, pentachlorophenol, permethrin, petroleum oils, phenkapton, phenothrin [(1R)-trans-isomer], phenthoate, phorate, phosalone, phosfolan, phosmet, phosnichlor, phosphamidon, phosphine, phoxim, phoxim-methyl, piperonyl butoxide, pirimetaphos, pirimicarb, pirimiphos-ethyl, pirimiphos-methyl, polychlorodicyclopentadiene isomers, polynactins, prallethrin, primidophos, proclonol, profenofos, promacyl, promecarb, propaphos, propargite, propetamphos, propoxur, prothidathion, prothiofos, prothoate, pymetrozine, pyraclofos, pyresmethrin, pyrethrins (pyrethrum), pyridaben, pyridalyl, pyridaphen thion, pyrimidifen, pyrimitate, pyriproxyfen, quinalphos, quinalphos-methyl, quinothion, quintiofos, R-1492, RA-17, resmethrin, rotenone, RU 15525, RU 25475, S421, sabadilla, schradan, silafluofen, SN 72129, sodium fluoride, sodium hexafluorosilicate, sodium selenate, sophamide, spinosad, spirodiclofen, spiromesifen, spirotetramat (BYI8330), SSI-121, sulcofuron-sodium, sulfluramid, sulfosulfuron, sulfotep, sulfur, sulprofos, SZI-12 1, taroils, tazimcarb, TDE, tebufenozide, tebufenpyrad, tebupirimfos, teflubenzuron, tefluthrin, temephos, TEPP, terallethrin, terbufos, tetrachlorvinphos, tetradifon, tetramethrin, tetramethrin [(1R)-isomers], tetrasul, theta-cypermethrin, thiacloprid, thiamethoxam, thicrofos, thiocarboxime, thiocyclam, thiodicarb, thiofanox, thiometon, thionazin, thioquinox, thiosultap-sodium, tolfenpyrad, tralomethrin, transfluthrin, transpermethrin, triamiphos, triarathene, triazamate, triazophos, trichlorfon, trichloronat, trifenofos, triflumuron, trimedlure, trimethacarb, vamidothion, XMC, xylylcarb, zeta-cypermethrin, zolaprofos, and ZXI 8901.

Preferred insecticides are chloronicontinyl insecticides of formula (I)

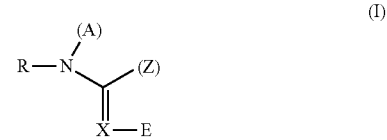

wherein
R is hydrogen, acyl, alkyl, aryl, aralkyl, heteroaryl or heteroarylalkyl;
A is hydrogen, acyl, alkyl, aryl, or a bifunctional group that is linked to Z;
E is NO$_2$, CN, or a halogenoalkylcarbonyl group;
X is —CR'= or =N—, wherein R' is hydrogen or a bifunctional group linked to Z;
Z is alkyl, —OR'', —SR'', or —NR''R'', or Z is a group linked to (i) the radical A or (ii) the radical X or (iii) both A and X;

provided that when E is CN, it is preferred that Z not be methyl and R not be a (6-chloro-3-pyridyl)methyl

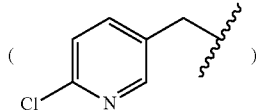 [SMILES: *Cc1ccc(Cl)nc1]

radical.

Certain CNI compounds of formula (I) are preferred. For example, when R is acyl, preferred embodiments are those in which R is formyl, alkylcarbonyl, or arylcarbonyl, or in which R is alkylsulfonyl, arylsulfonyl, or (alkyl)-(aryl)-phosphoryl, which may in turn be substituted.

The term acyl comprises the following definitions. By the term "$C_2$-$C_6$ alkanoyl" is meant straight or branched chain alkanoyl groups having from 2 to 6 carbon atoms. Examples of $C_2$-$C_6$ alkanoyl are acetyl, propanoyl, butanoyl, pentanoyl, hexanoyl, lauroyl, myristoyl, palmitoyl, stearoyl, eicosanoyl, lignoceroyl and isomeric forms thereof.

The term "$C_7$-$C_{11}$ aroyl" refers to benzoyl and 1- or 2-naphthoyl.

The term "$C_7$-$C_{16}$ aralkanoyl" refers to $C_1$-$C_6$ alkanoyl substituted with $C_6$-$C_{10}$ aryl such that the total number of carbon atoms is from 7 to 16. An example of $C_7$-$C_{11}$ aralkanoyl is phenacetyl.

The term "($C_1$-$C_6$ alkoxy)carbonyl" refers to straight or branched chain alkoxycarbonyl groups having from 1 to 6 carbon atoms in the alkoxy portion. Examples of ($C_1$-$C_6$ alkoxy)carbonyl are methoxycarbonyl, ethoxycarbonyl, propoxycarbonyl, butoxycarbonyl, pentyloxycarbonyl, hexyloxycarbonyl, and the isomeric forms thereof.

The term "($C_6$-$C_{10}$ aryloxy)carbonyl" refers to phenoxycarbonyl and 1- or 2-naphthoxycarbonyl, in which the aryl portion can optionally be further substituted with halogen, alkyl, alkoxy, alkoxycarbonyl, or nitro.

The term "carbamoyl" refers to an unsubstituted aminocarbonyl group.

The term "($C_1$-$C_6$ alkylamino)carbonyl" refers to straight or branched chain alkylamino-substituted carbonyl groups having from 1 to 6 carbon atoms in the alkylamino portion. Examples of ($C_1$-$C_6$ alkanoyl)amino are methylaminocarbonyl (also known as N-methylcarbamoyl), ethylamino-carbonyl, and the like. Such alkylaminocarbonyl groups can optionally be N-substituted with alkyl or aryl groups.

The term "($C_6$-$C_{10}$ arylamino)carbonyl" refers to phenylamino-carbonyl (or anilinocarbonyl) and 1- or 2-naphthylaminocarbonyl. Such arylaminocarbonyl groups can optionally be N-substituted with alkyl or aryl groups.

The term "($C_7$-$C_{16}$ aralkoxy)carbonyl" refers to ($C_1$-$C_6$ alkoxy)-carbonyl substituted with $C_6$-$C_{10}$ aryl such that the total number of carbon atoms in the aralkoxy portion is from 7 to 16. An example of ($C_7$-$C_{16}$ aralkoxy)carbonyl is benzyloxycarbonyl (also known as carbobenzoxy).

The term "$C_1$-$C_6$ alkylsulfonyl" refers to straight or branched chain alkylsulfonyl groups having from 1 to 6 carbon atoms. Examples of $C_1$-$C_6$ alkylsulfonyl are methylsulfonyl (also known as mesyl) and ethanesulfonyl.

The term "$C_1$-$C_6$ alkylsulfinyl" refers to straight or branched chain alkylsulfinyl groups having from 1 to 6 carbon atoms. Examples of $C_1$-$C_6$ alkylsulfinyl are methylsulfinyl and ethanesulfinyl.

The term "$C_6$-$C_{10}$ arylsulfonyl" refers to phenylsulfonyl and 1- or 2-naphthylsulfonyl, as well as optionally substituted forms such as toluene-sulfonyl (also known as tosyl).

The term "$C_6$-$C_{10}$ arylsulfinyl" refers to phenylsulfinyl and 1- or 2-naphthylsulfonyl, as well as optionally substituted forms such as toluene-sulfinyl (also known as tosyl).

If R is alkyl, preferred embodiments are $C_{1-10}$-alkyl, especially $C_{1-4}$-alkyl, specifically methyl, ethyl, i-propyl, sec- or t-butyl, which may in turn be substituted by one more halogen atoms. By the term halogen is meant F, Cl, Brand I.

If R is aryl, phenyl and naphthyl, especially phenyl are preferred. As used herein, the term "aryl" also refers to phenyl and naphthyl groups substituted with alkyl, alkoxy, halogen, hydroxy (including tautomeric oxo forms), alkoxycarbonyl, aryloxycarbonyl, cyano, and nitro as defined herein.

If R is aralkyl, preferred embodiments are phenylmethyl and phenylethyl. By the term "$C_7$-$C_{16}$ aralkyl" is meant $C_1$-$C_6$ alkyl substituted with $C_6$-$C_{10}$ aryl such that the total number of carbon atoms is from 7 to 16. Examples of $C_7$-$C_{16}$ aralkyl are benzyl, phenethyl, and naphthylmethyl.

R may be heteroaryl. By the term heteroaryl is meant a heterocycle having up to 10 ring atoms and N, O, S especially N as heteroatoms wherein the ring is unsaturated to provide an electronically aromatic system following Hückel's Rule. Heteroaryl may be a five- or six-membered aromatic groups having one or more ring heteroatoms, such as nitrogen, oxygen, and sulfur, and fused-ring analogs thereof. Heteroaryl may be substituted with hydroxy (including tautomeric oxo forms), halogen, alkyl, alkoxy, alkoxycarbonyl, or aryloxycarbonyl. Suitable heteroaryl groups include pyridyl, pyrimidyl, imidazolyl, and thiazolyl. Especially preferred embodiments include thienyl, furyl, thiazolyl, imidazolyl, pyridyl and benzothiazolyl rings. Heteroaryl may be further substituted with hydroxy (including tautomeric oxo forms), halogen, alkyl, alkoxy, alkoxycarbonyl, or aryloxycarbonyl. Suitable heteroaryl groups include pyridyl, pyrimidyl, imidazolyl, and thiazolyl.

R may be heteroarylalkyl. By the term heteroarylalkyl is meant a heteroaryl moiety attached to an alkyl radical. Examples include heterooarylmethyl and heteroarylethyl with the heteroaryl moiety having up to 6 ring atoms and N, O, S, especially N as heteroatoms.

Substituents which may be listed by way of example and preference are alkyl having preferably 1 to 4, in particular 1 or 2 carbon atoms, such as methyl, ethyl, n- and i-propyl and n-, i-, and t-butyl; alkoxy having preferably 1 to 4, in particular 1 or 2, carbon atoms, such as methoxy, ethoxy, n- and i-propyloxy and n-, i-, and t-butyloxy; alkylthio having preferably 1 to 4, in particular 1 or 2 carbon atoms, such as methylthio, ethylthio, n- and i-propylthio and n-, i-, and t-butylthio; halogenoalkyl having preferably 1 to 4, in particular 1 or 2 carbon atoms, and preferably 1 to 5, in particular 1 to 3, halogen atoms, the halogen atoms being identical or different and being preferably fluorine, chlorine, or bromine, especially fluorine, such as trifluoromethyl; hydroxyl; halogen, preferably fluorine, chlorine, bromine, and iodine, especially fluorine, chlorine, and bromine; cyano; nitro; amino; mono-alkyl- and dialkylamino having preferably 1 to 4, in particular 1 or 2, carbon atoms per alkyl group, such as methylamino, methyl-ethyl-amino, n- and i-propylamino and methyl-n-butylamino; carboxyl; carbalkoxy having preferably 2 to 4, in particular 2 or 3, carbon atoms, such as carbomethoxy and carboethoxy; sulfo (—$SO_3H$); alkylsulfonyl having preferably 1 to 4, in particular 1 or 2, carbon atoms, such as methylsulfonyl and ethylsulfonyl; arylsulfonyl having preferably 6 or 10 aryl carbon atoms, such as phenylsulfonyl, and also heteroarylamino and heteroarylalkylamino such as chloropyridylamino and chloropyridylmethylamino.

A preferably is hydrogen and optionally substituted radicals from the series acyl, alkyl, aryl, which preferably have the meanings given for R. A additionally represents a bifunctional group. There may be mentioned optionally substituted alkylene group having from 1 to 4 carbon atoms in particular from 1 to 2 carbon atoms. Substituents on the alkylene chain include those listed under the definition of R. The alkylene groups may be interrupted by heteroatoms N, O, or S.

Alternatively, A and Z may, together with the atoms to which they are attached, form a saturated or unsaturated heterocyclic ring. The heterocyclic ring can contain a further 1 or 2 identical or different heteroatoms and/or hetero-groups. Heteroatoms are preferably oxygen, sulfur or nitrogen, and hetero-groups are preferably N-alkyl, where the alkyl in the N-alkyl group preferably contains 1 to 4, in particular 1 or 2, carbon atoms. The alkyl group is preferably methyl, ethyl, n- and i-propyl and n-, i-, or t-butyl. The heterocyclic ring contains 5 to 7, preferably 5 or 6, ring members.

When A and Z together with the atoms to which they are attached will preferably form a heterocycle which includes imidazolidine, pyrrolidine, piperidine, piperazine, hexamethyleneimine, hexahydro-1,3,5-triazine, hexahydrooxodiazine, and morpholine, each of which may optionally be substituted by lower alkyl, preferably by methyl.

X preferably represents —CH═ or —N═.

Z represents the optionally substituted radicals alkyl, —OR″, —SR″, —NR″R″, where R″ and the substituents preferably have the meaning given above for the substituents of R.

When X is ═CR′, Z can form with X a saturated or unsaturated heterocyclic ring. The heterocyclic ring can contain a further 1 or 2 identical or different heteroatoms and/or hetero-groups. The heteroatoms are preferably oxygen, sulfur or nitrogen, and the hetero-groups N-alkyl, in which case the alkyl or N-alkyl group preferably contains 1 to 4, in particular 1 or 2, carbon atoms. As alkyl there may be mentioned methyl, ethyl, n- and i-propyl and n-, i-, and t-butyl. The heterocyclic ring contains 5 to 7, preferably 5 or 6, ring members. Examples of the heterocyclic ring which may be mentioned are pyrrolidine, piperidine, piperazine, hexamethyleneimine, morpholine, and N-methylpiperazine.

As compounds which may be used with very particular preference in accordance with the invention, mention may be made of compounds of the general formulas (II), (III), and (IV):

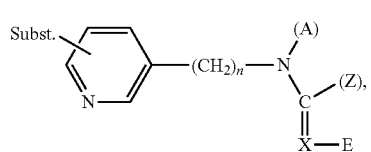

(II)

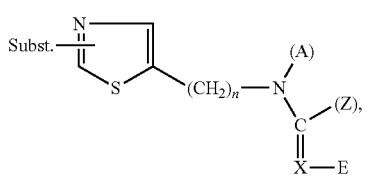

(III)

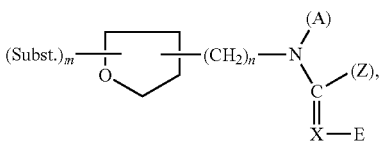

(IV)

in which
n represents 1 or 2,
m represents 0, 1 or 2,
Subst. represents one of the above-listed substituents for R, especially halogen, very particularly chlorine,
Particular emphasis is given to the compounds

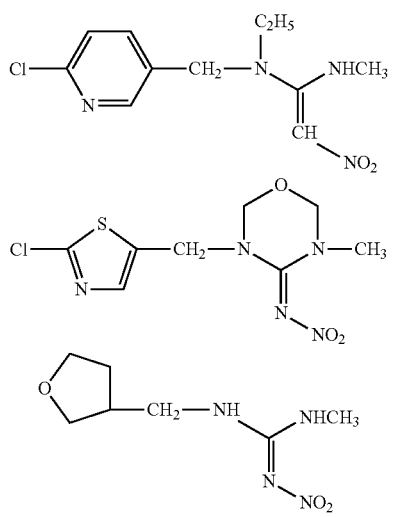

Furthermore, particular emphasis is given to the compounds

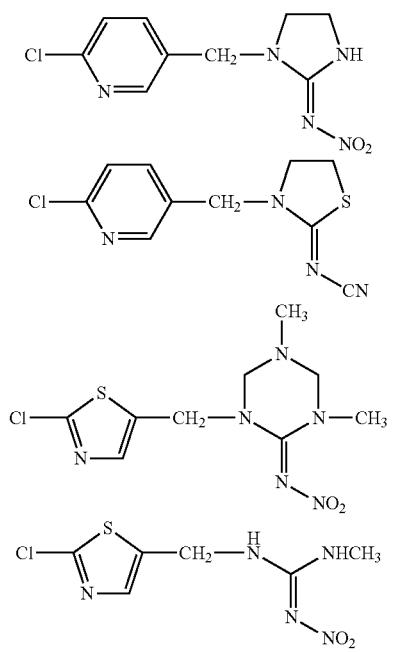

Compounds of formula (I) are known, for example, from European Offenlegungsschriften Nos. 580553, 464830, 428941, 425978, 386565, 383091, 375907, 364844, 315826, 259738, 254859, 235725, 212600, 192060, 163855, 154178, 136636, 303570, 302833, 306696, 189972, 455000, 135956, 471372, 302389; German Offenlegungsschriften Nos. 3639877, 3712307; Japanese Offenlegungsschriften Nos. 03220176, 02207083, 63307857, 63287764, 03246283, 049371, 03279359, 03255072; U.S. Pat. Nos. 5,034,524, 4,948,798, 4,918,086, 5,039,686, 5,034,404; PCT Applications No. WO 91/17659, 91/4965; French Application No. 2611114; Brazilian Application No. 8803621.

Other suitable agrochemically active compounds used according to this invention include herbicides. As used herein, the term "herbicide" broadly refers to compounds or compositions that are used as herbicides, as well as herbicide safeners and algicides. Chemical classes of herbicides include 1,2,4-triazinones, 1,3,5-triazines, alkanamides (acetamides), anilides, aryloxyalkanoic acids, aryloxyphenoxypropionates, benzamides (mi), benzamides (L), benzenedicarboxylic acids, benzofurans, benzoic acids (auxins), benzonitriles, benzothiadiazinones, benzothiazolones, carbamates (DHP), carbamates (mi), chloroacetamides, cyclohexanedione oximes, dinitroanilines, dinitrophenols, diphenyl ethers, diphenyl ethers (cbi), glycine derivatives, halogenated alkanoic acids, hydroxybenzonitriles, imidazolinones, isoxazoles, isoxazolidinones, N-phenylphthalimides, organoarsenics, oxadiazoles, oxazolidinediones, oxyacetamides, phenoxycarboxylic acids, phenyl carbamate herbicides, phenylpyrazole herbicides, phenylpyridazines, phosphinic acids, phos-phorodithioates, phthalamates, pyrazole herbicides, pyridazines, pyridazinones (PDS), pyridazinones (PSII), pyridines, pyridinecarbox-amides, pyridinecarboxylic acids, pyrimidindiones, pyrimidines, pyrimidinyl-oxybenzoics, pyrimidinyloxybenzoic analogs, quinolinecarboxylic acids, BI class IV: thiocarbamate, semicarbazones, sulfonylaminocarbonyl-triazolinones, sulfonylureas, tetrazolinones, thiadiazoles, thiocarbamates, triazoles, triazolinones, triazolopyrimidines, triketones, uracils, and ureas. Suitable herbicides include 2,3,6-TBA, 2,4,5-T, 2,4-D, 2,4-D-2-ethylhexyl, 2,4-DB, 2,4-D-dimethylammonium, 2,4-D-isopropyl, 2,4-D-isopropyl, 2,4-D-trolamine (2,4-D-triethanolamine), ACD 10614; ACD 10435, acetochlor, acifluorfen, acifluorfen-sodium, aclonifen, acrolein, AD 67, alachlor, alloxydim-sodium, ametryn, amicarbazone, amidosulfuron, amitrole, ammonium sulfamate, anilofos, asulam, atraton, atrazine, azafenidin, azimsulfuron, aziprotryne, barban, beflubutamid, benazolin, benazolin-ethyl, benfluralin, benfuresate, benoxacor, bensulfuron-methyl, bensulide, bentazone, benzobicyclon, benzofenap, benzoylprop, enzoylprop-ethyl, bifenox, bilanafos-sodium, bispyribac-sodium, borax, bromacil, bromobutide, bromofenoxim, bromoxynil, bromoxynil octanoate, bromoxynil-potassium, brompyrazon, butachlor, butafenacil, butenachlor, buthidazole, butralin, butroxydim, buturon, cafenstrole, calcium cyanamide, carbetamide, carfentrazone-ethyl, chlomethoxyfen, chloramben, chlorbromuron, chlorbufam, chlorfenac, chlorfenac-sodium, chlorfenprop, chlorfenprop-methyl, chlorfenprop, chlorfenprop-ethyl, chlorflurenol-methyl, chloridazon, chlorimuron-ethyl, chlornitrofen, chloroacetic acid, chloro-toluron, chloroxuron, chlorpropham, chlorsulfuron, chlorthal-dimethyl, chlorthiamid, cinidon-ethyl, cinosulfuron, clodinafop-propargyl, clofop, clofop-isobutyl, clomazone, clomeprop, clopyralid, cloquintocet-mexyl, cloransulam-methyl, credazine, cumyluron, cyanamide, cyanazine, cyclosulfamuron, cycloxydim, cycluron, cyhalofop-butyl, cyometrinil, daimuron, dazomet, desmedipham, desmetryn, di-allate, dicamba, dichlobenil, dichlormid, dichlorprop, dichlorprop-isoctyl, dichlorprop-P, diclofop, diclofop-methyl, diclosulam, diethatyl-ethyl; diethatyl, difenoxuron, difenzoquat metilsulfate, diflufenican, diflufenzopyr, dikegulac, dikegulac-sodium, dimefuron, dimepiperate, dimethachlor, dimethametryn, dimethipin, dimethylarsinic acid, dinitramine dinoseb, dinoseb acetate, dinoterb, diphenamid, dipropetryn, disul, disul-sodium, dithiopyr, diuron, DNOC, DSMA, eglinazine-ethyl, eglinazine, EL 177, endothal, ethalfluralin, ethametsulfuron-methyl, ethidimuron, ethofumesate, ethoxysulfuron, etobenzanid, fenchlorazole-ethyl, fenclorim, fenoprop, fenoprop-butotyl, fenoxaprop-ethyl, fenoxaprop, fenoxaprop-P, fenoxaprop-P-ethyl, fenthiaprop; fenthiaprop-ethyl, fentrazamide, fenuron, flamprop-methyl, flamprop-isopropyl, flamprop, flamprop-M-isopropyl, flamprop-M-methyl, flazasulfuron, florasulam, fluazifop-butyl, fluazifop-P, fluazifop-P-butyl, fluazolate, flucarbazone-sodium, fluchloralin, flufenacet, flumetsulam, flumiclorac-pentyl, flumioxazin, flumipropyn, fluometuron, fluorodifen, fluoroglycofen-ethyl, fluothiuron, flupoxam, flupropanate-sodium, flupyr-sulfuron-methyl-sodium, fluarazole, flurenol-butyl, fluridone, flurochloridone, fluroxypyr, fluroxypyr-meptyl, flurtamone, fluthiacet-methyl, fomesafen, foramsulfuron, fosamine-ammonium, furilazole, glufosinate-ammonium, glyphosate, glyphosate-ammonium, glyphosate-isopropylammonium, glyphosate-sodium, glyphosate-trimesium, halosulfuron-methyl, haloxyfop, haloxyfop-etotyl, haloxyfop-P, hexaflurate, hexazinone, imazamethabenz-methyl, imazamox, imazapic, imazapyr, imazapyr-isopropylammonium, imazaquin, imazethapyr, imazosulfuron, indanofan, iodosulfuron-methyl-sodium, ioxynil, ioxynil octanoate, ioxynil-sodium, isocarbamid, isocil, isomethiozin, isonoruron, isoproturon, isouron, isoxaben, isoxaflutole, isoxapyrifop, karbutilate, lactofen, lenacil, linuron, LS830556, maleic hydrazide, MCPA, MCPA-thioethyl, MCPB, MCPB-ethyl, mecoprop, mecoprop-P, medinoterb acetate, medinoterb, mefenacet, mefenpyr-diethyl, mefluidide, mesosulfuron-methyl, mesotrione, metamifop, metamitron, metazachlor, methabenzthiazuron, methazole, methiuron, methoprotryne, methoxyphenone, methyl isothiocyanate, methylarsonic acid, methyidymron, metobenzuron, metobromuron, metolachlor, meto-sulam, metoxuron, metribuzin, metsulfuron-, ethyl, MK-616, monalide, monolinuron, monuron, monuron-TCA, MSMA, naphthalic anhydride, naproanilide, napropamide, naptalam, NC-330, neburon, nicosulfuron, nitralin, nitrofen, nonanoic acid, norflurazon, oleic acid (fatty acids), orbencarb, oryzalin, oxabetrinil, oxadiargyl, oxadiazon, oxasulfuron, oxaziclomefone, oxyfluorfen, pendimethalin, penoxsulam, pentachlorophenol, pentanochlor, pentoxazone, perfluidone, pethoxamid, phen-isopham, phenmedipham, phenylmercury acetate, picolinafen, primi-sulfuron-methyl, prodiamine, profluralin, proglinazine-ethyl, proglinazine, prometon, prometryn, propachlor, propanil, propaquizafop, propazine, propham, propisochlor, propoxycarbazone-sodium, propyzamide, prosulfuron, pyraflufen-ethyl, pyrazolynate, pyrazosulfuron-ethyl, pyrazoxyfen, pyribenzoxim, pyributicarb, pyridate, pyriftalid, pyriminobac-methyl, pyrithiobac-sodium, quinclorac, quinmerac, quinoclamine, quizalofop-ethyl, quizalofop-P-ethyl, quizalofop-P-tefuryl, rimsulfuron, sebuthylazine, secbumeton, siduron, simazine, simetryn, S-metolachlor, SMY 1500, sodium chlorate, sulcotrione, sulfentrazone, sulfometuron-methyl, sulfosulfuron, tebuthiuron, tepraloxydim, terbacil, terbumeton, terbuthylazine, terbutryn, thenylchlor, thiazafluron, thiazopyr, thidiazimin, thifensulfuron-methyl, thiobencarb, 1-dichloroacetylazepane, tralkoxydim, tri-allate, triasulfuron, tribenuron-methyl, trichloroacetic acid, triclopyr, tridiphane, trietazine, trifloxysulfuron-sodium, trifluralin, and triflusulfuron-methyl.

Other suitable agrochemically active compounds used according to this invention include fungicides. Chemical classes of fungicides include amino acid amide carbamates, anilinopyrimidines, antibiotics, aromatic hydrocarbons, heteroaromatics, chloro/nitrophenyls, benzamides (F), benzenesulfonamides, benzimidazoles, benzimidazole precursors, benzotriazines, carboxamides, cinnamic acids, cyanoacetamide oximes, dicarboximides, dithiolanes, DMI: imidazoles, DMI: piperazines, DMI: pyrimidines, DMI: triazoles, enopyranuronic acid antibiotics, heteroaromatic hydroxyanilides, MBI: dehydratases, MBI: reductases, morpholine: morpholines, morpholine: spiroketalamines, multi-site: chloronitriles, multi-site: dimethyidithiocarbamates, multi-site: guanidines, multi-site: inorganics, multi-site: phthalimides, multi-site: quinones, multi-site: sulfamides, N-phenyl carbamate fungicides, organotin fungicides, phenylamide: acylalanines, phenylamide: butyrolactones, phenylamide: oxazolidinones, phenylpyrroles, phenylurea fungicides, phosphonates, phosphorothiolates, pyridazinone fungicides, pyrimidinamines, pyrimidinols, Qil, quinolines, SBI class IV: thiocarbamates, strobilurin analog: dihydrodioxazines, strobilurin type: imidazolinones, strobilurin type: methoxy-acrylates, strobilurin type: ethoxycarbamates, strobilurin type: oxazolidinediones, strobilurin type: oximinoacet-amides, strobilurin type: oximinoacetates, thiazolecarbox-amides, thiocarbamate fungicides, and thiophenecarboxamides. Suitable fungicides include 1,2-dichloropropane, 2-methoxyethylmercury chloride, 2-phenylphenol, 8-hydroxyquinoline sulfate, ampropylfos, anilazine, azaconazole, azoxystrobin, benalaxyl, benodanil, benomyl, benquinox, benthiavalicarb-isopropyl, binapacryl, biphenyl, bis(tributyltin) oxide, bitertanol, blasticidin-S, borax, boscalid, bromuconazole, bupirimate, buthiobate, captafol, captan, carbendazim, carboxin, carpropamid, CGA 80 000, chinomethionat, chlobenthiazone, chloraniformethan, chloroneb, chlorothalonil, chlozolinate, climbazole, copper oxychloride, copper sulfate, copper sulfate (tribasic), cuprous oxide, cyazofamid, cyflufenamid, cymoxanil, cyproconazole, cyprodinil, cyprofuram, dazomet, dichlofluanid, dichlone, dichlorophen, diclobutrazol, diclocymet, diclomezine, dicloran, diethofencarb, difenoconazole, difenzoquat metilsulfate, diflumetorim, dimethirimol, dimethomorph, dimoxystrobin, diniconazole, dinobuton, dinocap, diphenylamine, ditalimfos, dithianon, dodemorph, dodemorph acetate, dodine, drazoxolon, edifenphos, epoxiconazole, etaconazole, etem, ethaboxam, ethirimol, etridiazole, famoxadone, fenamidone, fenarimol, fenbuconazole, fenfuram, fenhexamid, fenitropan, fenoxanil, fenpiclonil, fenpropimorph, fentin acetate, fentin hydroxide, ferimzone, fluazinam, fludioxonil, flumorph, fluoroimide, fluotrimazole, fluoxastrobin, fluquinconazole, flusilazole, flusulfamide, flutolanil, flutriafol, folpet, fosetyl-aluminum, fuberidazole, furalaxyl, furametpyr, furconazole-cis, furmecyclox, glyodin, griseofulvin, halacrinate, hexachlorobenzene, hexaconazole, hymexazol, imazalil, imibenconazole, iminoctadine triacetate, iminoctadine tris(albesilate), ipconazole, iprodione, iprovalicarb, isoprothiolane, kasugamycin hydrochloride hydrate, kresoxim-methyl, mebenil, mepanipyrim, mepronil, mercuric chloride, metalaxyl, metalaxyl-M, metconazole, methasulfocarb, methfuroxam, methyl iodide, methyl isothiocyanate, metominostrobin, metsulfovax, mildiomycin, myclobutanil, myclozolin, natamycin, nitrothal-isopropyl, nuarimol, ofurace, oleic acid, fatty acids), oxabetrinil, oxadixyl, oxpoconazole fumarate, oxycarboxin, penconazole, pencycuron, pentachlorophenol, phenylmercury acetate, phenylmercury dimethyidithiocarbamate, phenylmercury nitrate, phosphonic acid, phthalide, picoxystrobin, polyoxin B, polyoxorim, potassium bicarbonate, potassium hydroxyquinoline sulfate, prochloraz, procymidone, propamocarb hydrochloride, propiconazole, proquinazid, prothiocarb; prothiocarb hydrochloride, prothioconazole, pyracarbolid, pyraclostrobin, pyrazophos, pyributicarb, pyrimethanil, pyroquilon, quinoclamine, quinoxyfen, quintozene, silthiofam, simeconazole, sodium bicarbonate, spiroxamine, SSF-109, sulfur, tebuconazole, tecnazene, tetraconazole, thiabendazole, thicyofen, thifluzamide, thiophanate, thiophanate-methyl, thiram, tiadinil, tolclofos-methyl, tolylfluanid, triadimefon, triadimenol, triamiphos, triazoxide, trichlamide, tricyclazole, trifloxystrobin, triflumizole, triforine, triticonazole, urbacid, validamycin, vinclozolin, zarilamid, ziram, and zoxamide.

Other suitable agrochemically active compounds used according to this invention include plant growth regulators, some of which can be grouped with other chemical classes. Chemical classes of plant growth regulators include aromatic hydrocarbons, chloro/nitrophenyls, auxins, benzoic acids (auxins), benzothiazolones, benzoylureas, carbamates, carbamates (mi), cytokinins, dinitroanilines, dithiolanes, DMI: triazoles, ethylene generators, gibberellins, phenoxycarboxylic acids, phenylureas, pyridazines, pyrimidinyl carbinols, quaternary ammoniums, synthetic auxins, and thiocarbamate fungicides. Suitable plant growth regulants include 1-naphthylacetic acid, 2-(1-naphthyl)acetamide, 2,4-D, 2,4-D-2-ethylhexyl, 2,4-D-dimethylammonium, 2,4-D-isopropyl, 2,4-D-isopropyl, 2,4-D-trolamine (2,4-D-triethanolamine), 2-hydrazinoethanol, 2-naphthyl-oxyacetic acid, 4-CPA, 4-indol-3-ylbutyric acid, 6-benzylaminopurine, ancymidol, aviglycine hydrochloride, azoluron, benazolin, benazolin-ethyl, buminafos, butralin, carbaryl, chlorfluazuron, chlorflurenol-methyl, chlormequat chloride, chlorphonium chloride, chlorpropham, clofencet-potassium, cloxyfonac, cyanamide, cyclanilide, cyromazine, daminozide, dicamba, difenzoquat metilsulfate, diflubenzuron, dikegulac, dikegulac-sodium, dimethipin, endothal, ethephon, ethychlozate, fenoxycarb, flumetralin, flurenol-butyl, flurprimidol, forchlorfenuron, gibberellic acid, glyphosine, inabenfide, indol-3-ylacetic acid, isoprothiolane, kinetin, maleic hydrazide, mefluidide, mepiquat chloride, methasulfocarb, N-m-tolyl-phthalamic acid, nonanoic acid, N-phenylphthalamic acid, paclobutrazol, piproctanyl bromide, prohexadione-calcium, propham, pydanon, intofen, tecnazene, teflubenzuron, tetcyclacis, thidiazuron, triapenthenol, tribufos, trinexapac, trinexapac-ethyl, uniconazole, uniconazole-P, and zeatin.

The following examples further illustrate details for the preparation and use of the compositions of this invention. The invention, which is set forth in the foregoing disclosure, is not to be limited either in spirit or scope by these examples. Those skilled in the art will readily understand that known variations of the conditions and processes of the following preparative procedures can be used to prepare these compositions. Unless otherwise noted, all temperatures are degrees Celsius and all percentages are percentages by weight.

EXAMPLES

Example 1—Liquid Phase Study

This study was done to determine that the medium viscosity is low when there is no active ingredient present.

The following solutions were prepared by adding ingredients and mixing using a Ross mixer. A 10 mL sample was added to a 50 mL graduated cylinder and the cylinder was shaken vigorously 20 times. The amount of foam was measured as the percent of the 50 mL volume. The viscosity of each sample was measured using Brookfield viscometer, LVTD, #3 spindle and a speed of 30 rpm with a setting of F=2 for all readings. Specific Gravity measurements were taken performed using a neat sample. Measurements of pH were taken of neat samples. Freezing and thawing temperatures were determined by placing samples in a −20° C. freezer overnight and then allowing the samples to warm. A freezing temperature was recorded when the sample became completely fluid with no noticeable ice crystals present. Tables 2 and 3 show the results of the liquid phase study. There was noticeably more foaming when Agnique PG 9116 was present. Agnique PG 9116 is a $C_9$-$C_{11}$ alkyl polyglycoside non-ionic surfactant with a 1.6% average degree of polymerization available from Cognis Chemicals, website http://www.cognis.com/cognis.html.

Example 2—Aqueous Suspension Phase Study

The procedures of Example 1 were performed on the compositions of Tables 4 and 5. The mixtures were prepared by mixing the ingredients first, followed by grinding the contents using a Silverson mixer. The lignin sulfonate medium is studied to show that generally the medium viscosity is low when there is no Al involved. It was observed that some formulation media foamed a lot when there is nonionic surfactant such as Agnique PG 9116 is present in the medium. Freezing and thawing points were not measured. Borrersperse NA is sodium lignosulfate (CAS number 8061-51-6) supplied by Lignotech. Hi-Sil 233 is Hydrated Amorphous Silica Gel, CAS number 112926-00-8, available from PPG Industries, Inc. Attagel 50 is an attapulgite clay available from Engelhard Corporation.

TABLE 2

Liquid Phase Study 1

| | 1 | 2 | 3 | 4 | 5 | 6 | 7 | 8 | 9 |
|---|---|---|---|---|---|---|---|---|---|
| Deionized Water | 96 g | 96 g | 96 g | 96 g | 96 g | 96 g | 96 g | 96 g | 96 g |
| Glycerin | 36 g | 36 g | 36 g | 36 g | 36 g | 36 g | 36 g | | 36 g |
| Borrersperse NA | 10.5 g | | | 10.5 g | | 10.5 g | 10.5 g | | |
| Agnique PG 9116 | | 1.5 g | | 1.5 g | 1.5 g | | 1.5 g | | |
| Potassium chloride | | | 12 g | | 12 g | 12 g | 12 g | | |
| Appearance | clear dark brown liquid, slight foam | clear colorless liquid with significant foam | clear colorless liquid, no foam | clear dark brown liquid, with significant foam | clear colorless liquid with significant foam | clear dark brown liquid, slight foam | clear dark brown liquid, with significant foam | clear colorless liquid, no foam | clear colorless liquid, slight foam |
| Foaming, vol. % | 8 | 80 | 0 | 76 | 60 | 10 | 80 | 0 | 0 |
| Viscosity, cps | 7.0 | 4.0 | 2.8 | 3.4 | 3.6 | 4.4 | 4.2 | 2.0 | 2.4 |
| Specific gravity | 1.098 | 1.067 | 1.119 | 1.098 | 1.117 | 1.144 | 1.136 | 1.000 | 1.067 |
| pH | 7.5 | 8.85 | 6.74 | 7.47 | 6.93 | 7.45 | 7.49 | 9.19 | 8.42 |
| Freeze/thaw Temp. C. | −8 C. | −6 C. | −12 C. | −9 C. | −13 C. | −13 C. | −13 C. | 0 | −6 C. |

TABLE 3

Liquid Phase Study 2

| | 10 | 11 | 12 | 13 | 14 | 15 | 16 |
|---|---|---|---|---|---|---|---|
| Deionized water | 96 g | 96 g | 96 g | 96 g | 96 g | 96 g | 96 g |
| Borrersperse NA | 10.5 g | | | 10.5 g | | 10.5 g | 10.5 g |
| Agnique PG 9116 | | 1.5 g | | 1.5 g | 1.5 g | | 1.5 g |
| Potassium chloride | | | 12 g | | 12 g | 12 g | 12 g |
| Appearance | clear dark brown liquid, slight foam | clear colorless liquid with significant foam | clear colorless liquid, no foam | clear dark brown liquid, with significant foam | clear colorless liquid with significant foam | clear dark brown liquid, slight foam | clear dark brown liquid with significant foam |
| Foaming, vol % | 14 | 84 | 0 | 78 | 94 | 16 | 90 |
| Viscosity | 4.0 | 2.6 | 2.6 | 3.6 | 2.8 | 3.0 | 4.0 |
| Specific gravity | 1.044 | 1.001 | 1.072 | 1.044 | 1.072 | 1.109 | 1.108 |
| pH | 7.63 | 8.78 | | 7.63 | 7.44 | 7.42 | 7.49 |
| Freeze/thaw Temp | 0° C. | 0° C. | −1° C. | 0° C. | −2° C. | −4° C. | −6° C. |

TABLE 4

Suspension Study 1

| | 17 | 18 | 19 | 20 | 21 | 22 | 23 | 24 | 25 | 26 | 27 |
|---|---|---|---|---|---|---|---|---|---|---|---|
| Deionized water | 96 g | 96 g | 96 g | 96 g | 96 g | 96 g | 96 g | 96 g | 96 g | 96 g | 96 g |
| Glycerin | 36 g | 36 g | 36 g | 36 g | 36 g | 36 g | 36 g | 36 g | 36 g | 36 g | 36 g |
| Borresperse NA | 10.5 g | 10.5 g | 10.5 g | 10.5 g | 10.5 g | 10.5 g | 10.5 g | 10.5 g | 10.5 g | 10.5 g | 10.5 g |
| Potassium chloride | | | | | | 12 g | 12 g | 12 g | 12 g | 12 g | 12 g |
| Aluminum oxide C | 1.2 g | | | 1.2 g | 1.2 g | | | | 1.2 g | 1.2 g | 1.2 g |
| Hi-Sil 233 | | 0.3 g | | 0.3 g | 0.3 g | 0.3 g | | 0.3 g | | 0.3 g | 0.3 g |
| Attagel 50 | | | 0.3 g | | 0.3 g | | 0.3 g | 0.3 g | | | 0.3 g |
| Appearance | hazy brown liquid with slight foam | clear brown liquid with slight foam | clear brown liquid with slight foam | hazy brown liquid with slight foam | hazy brown liquid with slight foam | clear brown liquid with slight foam | clear brown liquid with slight foam | clear brown liquid with slight foam | hazy brown liquid with slight foam | hazy brown liquid with slight foam | hazy brown liquid with slight foam |
| Foaming vol. % | 8 | 8 | 8 | 8 | 10 | 8 | 8 | 10 | 12 | 8 | 8 |
| Viscosity, cps | 5.8 | 7.8 | 9 | 4.2 | 5.2 | 5.6 | 5.6 | 3.6 | 5.8 | 4.8 | 4.4 |
| Specific gravity | 1.105 | 1.095 | 1.099 | 1.104 | 1.106 | 1.140 | 1.145 | 1.140 | 1.148 | 1.149 | 1.148 |
| pH | 7.61 | 7.63 | 7.66 | 7.59 | 7.65 | 7.34 | 7.45 | 7.4 | 7.35 | 7.32 | 7.4 |

TABLE 5

Suspension Study 2

| | 28 | 29 | 30 | 31 | 32 | 33 | 34 | 35 | 36 | 37 | 38 |
|---|---|---|---|---|---|---|---|---|---|---|---|
| Deionized water | 96 g | 96 g | 96 g | 96 g | 96 g | 96 g | 96 g | 96 g | 96 g | 96 g | 96 g |
| Borresperse NA | 10.5 g | 10.5 g | 10.5 g | 10.5 g | 10.5 g | 10.5 g | 10.5 g | 10.5 g | 10.5 g | 10.5 g | 10.5 g |
| Potassium chloride | | | | | | 12 g | 12 g | 12 g | 12 g | 12 g | 12 g |
| Aluminum oxide C | 1.2 g | | | 1.2 g | 1.2 g | | | | 1.2 g | 1.2 g | 1.2 g |
| Hi-Sil 233 | | 0.3 g | | 0.3 g | 0.3 g | 0.3 g | | 0.3 g | | 0.3 g | 0.3 g |
| Attagel 50 | | | 0.3 g | | 0.3 g | | 0.3 g | 0.3 g | | | 0.3 g |
| Appearance | hazy brown liquid with slight foam | clear brown liquid with slight foam | clear brown liquid with slight foam | hazy brown liquid with slight foam | hazy brown liquid with slight foam | clear brown liquid with slight foam | clear brown liquid with slight foam | clear brown liquid with slight foam | hazy brown liquid with slight foam | hazy brown liquid with slight foam | hazy brown liquid with slight foam |
| Foaming, vol. % | 14 | 14 | 14 | 18 | 16 | 16 | 16 | 16 | 16 | 16 | 16 |
| Viscosity, cps | 2.4 | 2 | 2.4 | 2.6 | 2.4 | 2.2 | 2 | 2.8 | 3 | 2.6 | 3.2 |
| Specific gravity | 1.051 | 1.045 | 1.045 | 1.04 | 1.054 | 1.102 | 1.109 | 1.109 | 1.114 | 1.115 | 1.117 |
| pH | 7.54 | 7.44 | 7.63 | 7.55 | 7.57 | 7.26 | 7.37 | 7.34 | 7.34 | 7.25 | 7.3 |

Example 3

Samples 39 through 42 were prepared from a wet-milled master batch of 328 g imidacloprid, 32 g, Borresperse NA, and 540 g water. The milling was carried out in a lab Dynomil milling device. After the particle size had reached 2.6 micron (<50% volume average), the resultant mill base was collected and subdivided. To each sample salt and/or glycerin was added to finish the formulations (Samples 39 to 42). The formulations demonstrated surprising compatibility with fertilizers tested (Table 6, 10-34-0, 3-18-18, and 6-24-6). A reference formula (Samples 43, Table 6) using the traditional surfactants alone was prepared for comparison. The fertilizer compatibility test in this invention is carried out to simulate the field test conditions (0.22 lb active ingredient per 5 gallons fertilizer); and the corresponding laboratory rate is 0.375 g active ingredient per 100 g fertilizer. Then the whole mixture is filtered through a screen of US Mesh 50, the net retained residues are measured and reported. The results demonstrated the superior compatibility of the Borresperse NA plus salt as a synergistic dispersant system to that using common surfactants. Morwet D425 is the sodium salt of alkylnaphthalenesulfonate formaldehyde polymer CAS #9084-06-4, alternatively identified with CAS numbers 68425-94-5, 83453-42-3, and 9008-63-3. Alkamuls EL 620 is a fatty acid ethoxylate non-ionic surfactant from Rhodia, Inc.

Samples 44 to 49 (Table 7) were prepared like those in Tables 4, 5 and 6. All ingredients including imidacloprid were mixed well before wet milling. The mixture was milled to an average particle size of 2.8 microns before discharge. Formulation specific gravity and viscosities were measured before testing for fertilizer compatibilities. It is surprising that the combined Ingredients of aluminum oxide, Attagel 50, and Hi Sil 233 further improved the integrity of the resultant formulations. Furthermore, fertilizer tests of these examples showed the significance of glycerin stabilizing the fertilizer dilutions. Lastly the controlled flocculation phenomena with shear thinning effect are clearly shown due to the presence of salt (e.g., potassium chloride).

TABLE 6

| | 39 | 40 | 41 | 42 | 43 |
|---|---|---|---|---|---|
| Imidacloprid | 31 | 31 | 31 | 31 | 31 |
| Morwet D425 | | | | | 2 |

TABLE 6-continued

|  | 39 | 40 | 41 | 42 | 43 |
|---|---|---|---|---|---|
| Alkamuls EL 620 |  |  |  |  | 1 |
| Borresperse NA | 3 | 3 | 3 | 3 |  |
| KCl |  | 2 | 2 |  |  |
| Zn sulfate | 0.2 |  |  | 0.2 |  |
| Glycerin |  |  | 13 | 14.8 |  |
| Water | 65.8 | 64 | 51 | 51 | 66 |
| Total (% weight) | 100 | 100 | 100 | 100 | 100 |
| Specific gravity, g/ml | 1.133 | 1.145 | 1.191 | 1.177 | 1.127 |
| Viscosity, cps, set | 83 | 56 | 64 | 54 | 12 |
| Viscosity, cps, stirred | 15 | 8 | 14 | 20 | 9.6 |
| 10-34-0 fertilizer + 50 mesh net retain, %* | 0 | 0 | 0 | 0 | 0 |
| 3-18-18 fertilizer + 50 mesh net retain, %* | 0.09 | 0.17 | 0.06 | 0.06 | 0.18 |
| 6-24-6 fertilizer + 50 mesh net retain, %* | 0.01 | 0.09 | 0.1 | 0.04 | 0.13 |

TABLE 7

Basic Formulation Study

|  | 44 | 45 | 46 | 47 | 48 | 49 |
|---|---|---|---|---|---|---|
| Imidacloprid | 47.1 g | 47.1 g | 47.1 g | 47.1 g | 47.1 g | 47.1 g |
| Borresperse NA | 3.50 g | 3.50 g | 3.50 g | 3.50 g | 3.50 g | 3.50 g |
| Agnique PG 9116 | 0.50 g | 0.50 g | 0.50 g | 0.50 g | 0.50 g | 0.50 g |
| Glycerin | 12.00 g | 12.00 g | 12.00 g |  |  |  |
| Aluminum oxide C | 0.40 g | 0.40 g |  | 0.40 g | 0.40 g |  |
| Attagel 50 | 0.10 g | 0.10 g | 0.20 g | 0.10 g | 0.10 g | 0.20 g |
| Potassium chloride | 4.00 g |  | 4.00 g | 4.00 g |  | 4.00 g |
| Hi-Sil 233 | 0.10 g | 0.10 g | 0.20 g | 0.10 g | 0.10 g | 0.20 g |
| Water | 32.00 g | 32.00 g | 32.00 g | 44.00 g | 44.00 g | 44.00 g |
| Results |  |  |  |  |  |  |
| Formulation Specific gravity, g/ml | 1.302 | 1.276 | 1.294 | 1.259 | 1.231 | 1.257 |
| Formulation viscosity, cps (set) | >4000 | 492 | >4000 | 2400 | 480 | >4000 |
| Formulation viscosity, cps (stirred) | 480 | 180 | 956 | 276 | 84 | 352 |
| Dilution in 342 ppm water* | <0.1 ml sediment, good resuspension after 24 hours | <0.1 ml sediment, good resuspension after 24 hours | <0.1 ml sediment, good resuspension after 24 hours | 0.1 ml sediment, some residue on resuspension | 0.1 ml sediment, some residue on resuspension | 0.1 ml sediment, some residue on resuspension |
| Dilution in 10-34-0 Fertilizer after pre-dilution with water** | good dispersion, good resuspension. | good dispersion, good resuspension | good dispersion, good resuspension | good dispersion, some sticky residues with resuspension | good dispersion, some sticky residues with resuspension | good dispersion, some sticky residues with resuspension |

*Water dilution test: 0.31 ml/95 g 342 ppm water
**1:2 dilution with water at 0.95 ml/99 g 10-34-0 fertilizer formulations containing nonionic surfactant in addition to the lignin sulfonate. Relatively speaking, the shear thinning in this systems is minimized, clearly due to the effect of the nonionic surfactants.

TABLE 8

|  | 50 | 51 |
|---|---|---|
| Imidacloprid | 25.0 | 25.0 |
| Morwet D425 | 2.0 |  |
| Geropon T 36 |  | 2.25 |
| Alkamul EL620 | 1.0 |  |
| APG 9116 |  | 0.5 |
| Vangel B | 0.5 | 0.3 |
| Hi Sil 233 |  | 0.2 |
| Kelzan | 0.5 | 0.5 |
| Water | 71.0 | 71.25 |
| Total | 100 | 100 |
| Specific gravity, g/ml | 1.065 | 1.004 |

Example 4

Two reference formulations (Table 8, Samples 50 and 51) with 25 weight % imidacloprid in 300 g batch were prepared in traditional suspension concentrate technology using standard wet-milling technique. All ingredients except Keizan (xanthan gum) were charged to a container beforehand and pre-ground using a rotary Silverson mixer followed by wet milling. The milling was carried out in a lab Dynomil apparatus until the particle size reached 2.5 micron (<50% volume average). To finish the formulation, Keizan was post added to the discharged mill bases.

Samples 52 to 54 (Table 9) are formulations containing 25 weight % insecticide with various salts; Samples 55 to 58 (Table 10) are formulations with various lignin sulfonate dispersant combinations. Shear thinning effect is prominent throughout the examples. Samples 59 to 62 (Table 11) are TABLE 8-continued

|  | 50 | 51 |
|---|---|---|
| Viscosity*, cps (set) | 2544 | 3208 |
| Viscosity*, cps (stirred) | 2496 | 3104 |

TABLE 9

|  | 52 | 53 | 54 |
|---|---|---|---|
| Imidacloprid | 25.00 | 25.00 | 25.00 |
| Borresperse NA | 2.50 | 2.50 | 2.50 |
| Glycerin | 8.00 | 8.00 | 8.00 |
| Aluminum oxide C | 0.30 | 0.30 | 0.30 |
| Attagel 50 | 2.50 | 2.50 | 2.50 |
| Hi-Sil 233 | 1.50 | 1.50 | 1.50 |

TABLE 9-continued

|  | 52 | 53 | 54 |
|---|---|---|---|
| Sodium sulfate | 3 | | |
| Calcium chloride | | 0.5 | |
| Zinc sulfate | | | 0.5 |
| Water | 57.2 | 59.7 | 59.7 |
| Total | 100 | 100 | 100 |
| Specific gravity, g/ml | 1.159 | 1.186 | 1.168 |
| Viscosity, cps, set | 2280 | 2300 | 1040 |
| Viscosity, cps, stirred | 1160 | 1648 | 864 |

TABLE 10

|  | 55 | 56 | 57 | 58 |
|---|---|---|---|---|
| Imidacloprid | 25.00 | 25.00 | 25.00 | 25.00 |
| Borresperse NA | 1.50 | 1.50 | 1.50 | 1.50 |
| Glycerin | 8.00 | 8.00 | 8.00 | 8.00 |
| Aluminum oxide C | 0.30 | 0.30 | 0.30 | 0.30 |
| Attagel 50 | 2.50 | 2.50 | 2.50 | 2.50 |
| Hi-Sil 233 | 1.50 | 1.50 | 1.50 | 1.50 |
| Potassium chloride | 3 | 3 | 3 | 3 |
| Ultrazine CA | 1 | | | |
| Supragil WP | | 1 | | |
| Geropon SDS | | | 1 | |
| Lignosperse AGK 200 | | | | 1 |
| Water | 57.2 | 57.2 | 57.2 | 57.2 |
| Total | 100 | 100 | 100 | 100 |
| Specific gravity, g/ml | 1.183 | 1.18 | 1.185 | 1.183 |

TABLE 10-continued

|  | 55 | 56 | 57 | 58 |
|---|---|---|---|---|
| Viscosity, cps, set | 4040 | 10160 | 4120 | 3320 |
| Viscosity, cps, stirred | 3064 | 8560 | 3332 | 1044 |

TABLE 11

|  | 59 | 60 | 61 | 62 |
|---|---|---|---|---|
| Imidacloprid | 25.00 | 25.00 | 25.00 | 25.00 |
| Borresperse NA | 1.50 | 1.50 | 1.50 | 1.50 |
| Glycerin | 8.00 | 8.00 | 8.00 | 8.00 |
| Aluminum oxide C | 0.30 | 0.30 | 0.30 | 0.30 |
| Attagel 50 | 2.50 | 2.50 | 2.50 | 2.50 |
| Hi-Sil 233 | 1.50 | 1.50 | 1.50 | 1.50 |
| Potassium chloride | 3 | 3 | 3 | 3 |
| Pluronic P 65 | 1 | | | |
| Iconol DA-6 | | 1 | | |
| Soprophor 796P | | | 1 | |
| Alkamul EL-620 | | | | 1 |
| Water | 57.2 | 57.2 | 57.2 | 57.2 |
| Total | 100 | 100 | 100 | 100 |
| Specific gravity, g/ml | 1.176 | 1.176 | 1.184 | 1.18 |
| Viscosity, cps, set | 8460 | 3320 | 1920 | 1780 |
| Viscosity, cps, stirred | 13200 | 2744 | 1624 | 1432 |

Example 5

Samples 50-62 were tested for fertilizer compatibility. Three fertilizers known for their harsh compatibility with many pesticides used in the filed were selected for testing purposes. They are (N—P—K) 10-34-0, 3-18-18 and 6-24-6. The same tank mixing method as in Table 6 was used and the results are compared in Table 12. It is clear that the new technology from this invention is superior to the traditional suspension concentrate in the area of fertilizer compatibility. A commercial pesticide formulation, Admire 2F, is included in the test. It is known that Admire 2F is made with old suspension concentrate technology.

TABLE 12

|  | 50 (ref) | 51 (ref) | Admire 2F (control) | 52 | 53 | 54 | 55 | 56 | 57 | 58 | 59 | 60 | 61 | 62 |
|---|---|---|---|---|---|---|---|---|---|---|---|---|---|---|
| 10-34-0 fertilizer + 50 mesh net retain, %* | 1.92 | 1.26 | 1.31 | 0.30 | 0.05 | 0.00 | 0.16 | 0.14 | 0.06 | 0.20 | 0.14 | 0.00 | 0.16 | 0.00 |
| 3-18-18 fertilizer + 50 mesh net retain, %* | 1.65 | 0.62 | 0.27 | 0.16 | 0.19 | 0.13 | 0.15 | 0.54 | 0.24 | 0.05 | 0.03 | 0.09 | 0.12 | 0.05 |
| 6-24-6 fertilizer + 50 mesh net retain, %* | 2.42 | 1.87 | 1.28 | 0.32 | 0.35 | 0.19 | 0.43 | 0.46 | 0.43 | 0.62 | 0.20 | 0.22 | 0.45 | 0.55 |

Example 6

Reference Sample 63 as indicated in Table 13 was prepared in the same manner as in Samples 50-51. The Reference Sample, along with the Samples 64-71 in Tables 14-15 were tested for fertilizer compatibility as indicated in Table 16.

TABLE 13

|  | 63 |
|---|---|
| Imidacloprid | 43.32 |
| Soprophor S25 | 1.5 |
| Atlox 4913 | 4.5 |
| Glycerin | 14 |
| Proxel GXL | 0.25 |
| Hi-Sil 233 | 0.1 |

TABLE 13-continued

| | 63 |
|---|---|
| Antifoam 8830 FG | 0.1 |
| Water | 36.23 |
| Total | 100 |
| Specific gravity, g/ml | 1.229 |
| Viscosity, cps, stirred | 612 |

TABLE 14

| | 64 | 65 | 66 | 67 |
|---|---|---|---|---|
| Imidacloprid | 43.30 | 43.30 | 43.30 | 43.30 |
| Norlig 11 D | 4.00 | 4.00 | | |
| Diwatex S-3 | | | 4.00 | 4.00 |
| Glycerin | 14.00 | 14.00 | 14.00 | 14.00 |
| Aluminum oxide C | 0.40 | 0.40 | 0.40 | 0.40 |
| Attagel 50 | 0.30 | 0.30 | 0.30 | 0.30 |
| Zinc sulfate | | 0.50 | | 0.50 |
| Potassium chloride | 4.00 | | 4.00 | |
| Hi-Sil 233 | 0.30 | 0.30 | 0.30 | 0.30 |
| Proxel GXL | 0.20 | 0.20 | 0.20 | 0.20 |
| Deionized water | 33.50 | 37.00 | 33.50 | 37.00 |
| Total | 100 | 100 | 100 | 100 |
| Specific gravity, g/ml | 1.295 | 1.256 | 1.284 | 1.242 |
| Viscosity, cps, set | 11840 | 4320 | 5480 | 19640 |
| Viscosity, cps, stirred | 7300 | 712 | 436 | 424 |

TABLE 15

| | 68 | 69 | 70 | 71 |
|---|---|---|---|---|
| Imidacloprid | 43.88 | 43.88 | 43.88 | 43.88 |
| Borresperse NA | 3.5 | 3.5 | 3.5 | 3.5 |
| Morwet D425 | 0.5 | 0.5 | 0.5 | 0.5 |
| Glycerin | 14 | 14 | 14 | 14 |
| Aluminum oxide C | 0.4 | 0.4 | 0.4 | 0.4 |
| Attagel 50 | 0.3 | 0.3 | 0.3 | 0.3 |
| Potassium chloride | 3 | | | |
| Sodium chloride | | 3 | | |
| Zinc sulfate | | | 0.5 | |
| Magnesium chloride | | | | 0.5 |
| Proxel GXL | 0.1 | 0.1 | 0.1 | 0.1 |
| Hi-Sil 233 | 0.3 | 0.3 | 0.3 | 0.3 |
| Antifoam 8830 FG | 0.3 | 0.3 | 0.3 | 0.3 |
| Water | 33.72 | 33.72 | 36.22 | 36.22 |
| Total | 100 | 100 | 100 | 100 |
| Specific gravity, g/ml | 1.281 | 1.286 | 1.261 | 1.254 |
| Viscosity, cps, set | 728 | 604 | 180 | 400 |
| Viscosity, cps, stirred | 188 | 176 | 60 | 128 |

TABLE 16

| 43% formulations | 63 | 64 | 65 | 66 | 67 | 68 | 69 | 70 | 71 |
|---|---|---|---|---|---|---|---|---|---|
| 342 ppm hard water + 50 mesh net retain, % | 0 | 0 | 0 | 0 | 0 | 0.04 | 0.07 | 0.02 | 0.00 |
| 10-34-0 fertilizer + 50 mesh net retain, % | 1.65 | 0.94 | 0.01 | 0.70 | 0.17 | 0.83 | 0.50 | 0.85 | 0.81 |
| 6-24-6 fertilizer + 50 mesh net retain, % | 0.43 | 0.05 | 0.16 | 0.69 | 0.14 | 0.29 | 0.29 | 0.40 | 0.75 |
| Formulation diluted with water 1:1 beforehand | | | | | | | | | |
| 10-34-0 fertilizer + 50 mesh net retain, % | 1.02 | 0 | 0 | 0 | 0 | 0.48 | 0.21 | 0.18 | 0.08 |
| 6-24-6 fertilizer + 50 mesh net retain, % | 0.6 | 0.024 | 0.032 | 0.014 | 0.011 | 0.16 | 0.13 | 0.29 | 0.10 |

Example 7

Preparation of Sample 68 in industrial batch scale. An industrial batch of high concentration imidacloprid suspension concentrate (550 g/l) was manufactured as follows. Charged to a mixing vessel of 150 gallon (568 liter) capacity in the order listed, water, 246 lb (112 kg); Borresperse NA, 30 lb (14 kg); Morwet D425, 4.3 lb (2.0 kg); glycerin, 120.5 lb (55 kg); aluminum oxide, 3.44 lb (1.6 kg); Attagel 50, 2.6 lb (1.2 kg); Hi-Sil 233, 2.6 lb (1.2 kg); Proxel GXL, 0.9 lb (0.41 kg); and Antifoam 8830 FG, 2.6 lb (1.2 kg). The ingredients were then well mixed followed by addition of 377 lb (171 kg) imidacloprid technical. Wet milling was carried out in a bead mill with a 5 liter chamber. Zirconium beads of 1.4 mm diameter were used. The ground formulation mill base was then discharged after the particle size reached <50% volume average of 2.75 microns. To the recovered mill base (762 lb, or 346 kg) was added 43.5 lb (19.7 kg) of water, 25 lb (11.3 kg) potassium chloride and 0.87 lb (0.39 kg) FD&C Blue 1 dye to complete the final formulation. The product afforded the following properties, specific gravity of 1.282, set viscosity, 728 cps and stirred viscosity, 188 cps. The initial viscosity was surprisingly low; however, given time the viscosity was found to have increased after 4 weeks at room temperature to a set viscosity of 1040 cps, stirred viscosity 80 cps; another sample after 4 weeks at 40 C provided a set viscosity of 3130 cps; stirred viscosity, 112 cps).

Example 8

The product of Example 7 was mixed with various liquid fertilizers under laboratory conditions. 500 mL of the following liquid fertilizers were placed into a clear container: local tap water; 7-30-3; 7-26-0-8; and 10-34-0. Admire 2F and Sample 68 were added at rates below for a 20 grams per acre application of imidacloprid to the soil. This represented about 3.1 mL of Admire 2F per 500 mL fertilizer and about 1.3 mL of Sample 68 per 500 mL fertilizer. Combinations were inverted four times and left to stand for 10 minutes. Observations were made immediately after inversion and after standing for 10 minutes. If combinations were not in solution after 10 minutes, an additional 250 mL of water was added to aid the product's entry into solution. Combination was inverted an additional four times and observations were taken after 10 minutes of standing. The following results shown in Tables 17-22 were obtained.

TABLE 17

| (Mixing with water) | Initial mixing | +10 minutes standing | +10 min. + 250 mL water |
|---|---|---|---|
| Admire 2F | Mixed into solution No scum layer No initial precipitates Foam | Normal product settling Foam | Not necessary |
| Sample 16 | Mixed into solution No scum layer No initial precipitates No foam | Normal product settling No foam | Not necessary |

TABLE 18

| Mix with 7-30-3 | Initial mixing | +10 minutes standing | +10 min. + 250 mL water |
|---|---|---|---|
| Admire 2F | Mixed into suspension of suspended bodies No scum layer nor initial precipitates No foam | Normal product settling | Addition of water did not change mixture |
| Sample 68 | Mixed into suspension of suspended bodies No scum layer No initial precipitates No foam | Normal product settling | Addition of water did not change mixture |

TABLE 19

| Mix with 7-26-0-8 | Initial mixing | +10 minutes standing | +10 min. + 250 mL water |
|---|---|---|---|
| Admire 2F | Mixed into suspension of suspended bodies No scum layer No initial precipitates No foam | Suspended bodies dissolved into a true solution No settling | — |
| Sample 68 | Mixed into suspension of suspended bodies No scum layer No initial precipitates No foam | Suspended bodies dissolved into a true solution No settling | — |

TABLE 20

| Mix with 10-34-0 | Initial mixing | +10 minutes standing | +10 min. + 250 mL water |
|---|---|---|---|
| Admire 2F | Mixed into suspension of suspended bodies Scum layer No initial precipitates No foam | Product settled out | Addition of water did not change mixture |
| Sample 68 | Mixed into suspension of suspended bodies No scum layer No initial precipitates No foam | Product settled out | Addition of water did not change mixture |

TABLE 21

| Mix with 5-17-0 | Initial mixing | +10 minutes standing | +10 min. + 250 mL water |
|---|---|---|---|
| Admire 2F | Mixed into suspension of suspended bodies Scum layer No precipitates No foam | Product settled out | — |
| Sample 68 | Mixed into a true solution No scum layer No precipitates No foam | Normal product settling | — |

TABLE 22

| | Initial mixing | +10 minutes standing | +10 min. + 250 mL water |
|---|---|---|---|
| Admire 2F | Mixed into suspension of suspended bodies No scum layer No precipitates No foam | Product settled out | — |
| AMSI 302 550SC | Mixed into a true solution No scum layer No precipitates No foam | Normal product settling | — |

Example 9

Solid insecticides, fungicides, and their mixture suspension concentrates (SC) were prepared using the same procedures as detailed in Example 3. The insecticides and fungicides encompass not only CNI compounds but a wide variety of other chemistries, yet the resultant suspensions surprisingly showed the same pattern of stability and induced shear thinning (Table 23). All samples showed the same fertilizer compatibility (Table 24).

TABLE 23

| | 72 | 73 | 74 | 75 | 76 | 77 | 78 |
|---|---|---|---|---|---|---|---|
| Imidacloprid | | | | | | | 32.80 |
| Trifloxystrobin | | | | | | | 14.10 |
| Clothianidin | 46.55 | | | | | 23.30 | |
| Carbaryl | | 30.00 | | | | | |
| Thiodicarb | | | 35.00 | | | 17.50 | |
| Aldicarb | | | | 40.00 | | | |
| BYI 8330 (spirotetramat) | | | | | 23.00 | | |

TABLE 23-continued

|  | 72 | 73 | 74 | 75 | 76 | 77 | 78 |
|---|---|---|---|---|---|---|---|
| Borresperse NA | 4.00 | 3.00 | 3.00 | 9.00 | 3.00 | 3.50 | 3.80 |
| Morwet D425 | 0.50 | 0.20 | 0.30 | 0.50 | 0.50 | 0.40 | 0.50 |
| Citric Acid |  |  |  | 0.10 |  |  |  |
| Glycerin | 8.00 | 16.00 | 12.00 | 10.00 | 16.00 | 10.00 | 8.00 |
| Potassium chloride | 2.00 | 8.00 | 4.00 | 6.50 | 4.00 | 3.00 | 2.00 |
| Aluminum oxide | 0.40 | 0.80 | 0.40 | 0.50 | 0.50 | 0.40 | 0.40 |
| Attagel 50 | 0.20 | 0.30 | 0.50 | 0.10 | 1.20 | 0.35 | 0.30 |
| Hi Sil 233 | 0.30 | 1.00 | 1.00 | 0.50 | 1.00 | 0.65 | 0.20 |
| Antifoam 8830FG | 0.30 | 0.30 | 0.30 | 0.15 | 0.20 | 0.30 | 0.20 |
| Proxel GXL | 0.10 | 0.10 | 0.10 | 0.10 | 0.10 | 0.10 | 0.10 |
| Water | 37.65 | 40.30 | 43.40 | 32.55 | 50.50 | 40.50 | 37.60 |
|  | 100.00 | 100.00 | 100.00 | 100.00 | 100.00 | 100.00 | 100.00 |
| Special gravity | 1.30 | 1.20 | 1.23 | 1.25 | 1.20 | 1.25 | 1.29 |
| Viscosity, set | 2264 | 2332 | 1464 | 1550 | 1215 | 1650 | 1320 |
| Viscosity, stirred | 532 | 228 | 210 | 330 | 255 | 345 | 264 |

TABLE 24

Fertilizer test results

| 3-18-18 fertilizer + 50 mesh net retain, % | 0.15 | — | 0.48 | — | 0.21 | 0.18 | — |
|---|---|---|---|---|---|---|---|

Example 10

Solid insecticides, fungicides, and their mixture suspension concentrates (SC) were prepared using the same procedures as detailed in Example 3 and then further mixed with emulsifiable concentrate (EC) of other insecticides or fungicides to form resultant suspoemulsions (SE). The insecticides and fungicides encompass a wide variety of chemistries, yet the resultant suspoemulsions surprisingly showed the same pattern of physical stability and induced shear thinning (Table 25). All samples showed the same fertilizer compatibility (Table 26).

TABLE 25

|  | 79 | 80 | 81 |
|---|---|---|---|
| Tebuconazole | 9.20 |  |  |
| Trifloxystrobin |  | 38.00 | 19 |
| Prothioconazole tech | 9.2 |  |  |
| Clothianidin |  |  | 23.3 |
| Ufoxane 3 A |  | 4.50 | 2.3 |
| Borresperse NA | 3.5 |  | 2 |
| Morwet D425 | 0.50 | 0.00 | 0.25 |
| Glycerin | 14.00 | 12.00 | 10 |
| Potassium chloride | 3.00 | 4.00 | 3 |
| Aluminum oxide | 0.40 | 0.40 | 0.4 |
| Attagel 50 | 0.50 | 0.20 | 0.2 |
| Hi Sil 233 | 0.30 | 1.00 | 0.65 |
| Antifoam 8830FG | 0.30 | 0.30 | 0.3 |
| Proxel GXL | 0.10 | 0.10 | 0.1 |
| Water | 59 | 39.50 | 38.5 |
| Total | 100.00 | 100.00 | 100.00 |
| Special gravity | 1.137 | 1.23 | 1.25 |
| Viscosity, set | 550 | 1350 | 1345 |
| Viscosity, stirred | 252 | 420 | 355 |

TABLE 26

Fertilizer test results

| 3-18-18 fertilizer + 50 mesh net retain, % | — | 0.56 | 0.14 |
|---|---|---|---|

Example 11

Solid insecticides, fungicides and their mixture suspension concentrate (SC) were prepared using the same procedures as detailed in Example 3, and then further mixed with emulsifiable concentrates (EC) of other insecticides or fungicides to form suspoemulsions (SE). The insecticides and fungicides encompass a wide variety of chemistry, yet the resultant suspoemulsions surprisingly showed the same pattern of physical stability and induced shear thinning (Table 27). All samples showed the same fertilizer compatibility (Table 28).

TABLE 27

|  | 82 | 83 | 84 |
|---|---|---|---|
| Imidacloprid |  |  | 16.10 |
| Clothianidin |  | 35.59 |  |
| Cyfluthrin |  | 9.93 | 16.10 |
| Trifloxystrobin | 19.00 |  |  |
| Propiconazole | 36.70 |  |  |
| Ufoxane 3 A | 2.30 |  |  |
| Borresperse NA |  | 4.00 | 3.50 |
| Morwet D425 |  | 0.50 | 0.50 |
| Glycerin | 6.00 | 8.00 | 12.00 |
| Potassium chloride | 2.00 | 3.00 | 5.00 |
| Aluminum oxide | 0.20 | 0.40 | 0.35 |
| Attagel 50 | 0.10 | 0.60 | 1.20 |
| Hi Sil 233 | 0.50 | 0.50 | 1.00 |
| Antifoam 8830FG | 0.15 | 0.40 | 0.30 |
| Proxel GXL | 0.05 | 0.10 | 0.10 |
| Water | 19.80 | 31.98 | 37.35 |
| Aromatic A-150 | 9.20 |  |  |
| Methylene chloride |  | 2.00 | 2.00 |
| Soprophor FLK | 4.00 |  |  |
| Pluraflo E5B |  | 2.00 | 1.50 |
| Atlox 4912 |  | 1.00 | 3.00 |
| Total | 100 | 100 | 100 |
| Special gravity | 1.156 | 1.228 | 1.25 |
| Viscosity, stirred | 220 | 430 | 250 |
| Viscosity, set | 750 | 2250 | 1540 |

TABLE 28

| Fertilizer test results | | | |
|---|---|---|---|
| 3-18-18 fertilizer + 50 mesh net retain, % | 0.44 | 1.02 | 0 |
| Formulation Diluted with Water 1:1 Beforehand | | | |
| 3-18-18 fertilizer + 50 mesh net retain, % | 0 | 0.33 | 0 |

Example 12

Suspension concentrate mixture formulations of insecticides ethiprole, fipronil, and imidacloprid were prepared using essentially the same procedure as described in Example 3, and fertilizer compatibility tests were conducted. Each SC formulation contained 200 g/L of the active compounds and surprisingly exhibited very good compatibility with an NPK plus iron fertilizer (Wuxal) (Tables 29 and 30).

TABLE 29

| | 85 | 86 |
|---|---|---|
| Ethiprole | 8.33 | |
| Imidacloprid | 8.33 | 8.31 |
| Fipronil | | 8.31 |
| Borresperse NA | 4.00 | 2.91 |
| Morwet D425 | 0.58 | 0.42 |
| Propylene glycol | 14.57 | 11.63 |
| Potassium chloride | 3.33 | 2.49 |
| Aluminum oxide | 0.58 | 0.33 |
| Attagel 50 | 0.33 | 0.25 |
| Tixosil 38 | 0.33 | 0.25 |
| Silicone antifoam | 0.33 | 0.25 |
| Proxel GXL | 0.17 | 0.08 |
| Water | 59.12 | 64.77 |
| Total | 100.00 | 100.00 |
| Special gravity | 1.14 | 1.14 |
| Dynamic viscosity at 7.5 per sec, mPa · s | 18 | 19 |
| Dynamic viscosity at 20 per sec, mPa · s | 16 | 16 |
| Dynamic viscosity at 100 per sec, mPa · s | 13 | 13 |

TABLE 30

| Fertilizer test results | | |
|---|---|---|
| 8-8-6 plus Fe fertilizer + 50 mesh retain, % | 0 | 0 |

Example 13

Suspension concentrates of herbicides and their mixtures were prepared using the procedures detailed in Example 3. The herbicides encompass a wide variety of chemistry yet the resultant suspensions surprisingly showed not only the same pattern of stability and induced shear thinning (Table 31) but also the same fertilizer compatibility (Table 32).

TABLE 31

| | 87 | 88 | 89 |
|---|---|---|---|
| Metribusin | 40 | | |
| Flufenacet | | 40 | |
| Isoxaflutole | | | 46 |
| Borresperse NA | 4 | 4 | 4 |
| Morwet D425 | 0.5 | 0.5 | 0.5 |
| Glycerin | 16 | 16 | 16 |
| Potassium chloride | 6 | 6 | 6 |
| Aluminum oxide | 0.4 | 0.4 | 0.4 |
| Attagel 50 | 0.2 | 0.2 | 0.3 |
| Hi Sil 233 | 0.4 | 0.4 | 1 |
| Antifoam 8830FG | 0.3 | 0.3 | 0.3 |
| Proxel GXL | 0.1 | 0.1 | 0.1 |
| Water | 32.1 | 32.1 | 25.4 |
| Total | 100 | 100 | 100 |
| Special gravity | 1.175 | 1.18 | 1.23 |
| Viscosity, set | 6800 | 7000 | 15800 |
| Viscosity, stirred | 3000 | 3000 | 2200 |

TABLE 32

| Fertilizer test results | | | |
|---|---|---|---|
| 32-0-0 fertilizer + 50 mesh retain, % | 0.15 | 0 | 0.12 |

Example 14

Solid herbicides and their mixed suspension concentrates (SC) were prepared separately with the same procedures as detailed in Example 3 and then further mixed with emulsifiable concentrates (EC) of other herbicides to form resultant suspoemulsions (SE). The insecticides encompass a wide variety of chemistry, yet the resultant suspoemulsions surprisingly showed the same pattern of physical stability and induced shear thinning (Table 33). All samples showed the same fertilizer compatibility (Table 34).

TABLE 33

| | 90 | 91 | 92 |
|---|---|---|---|
| Metribusin | | | 20 |
| Isoxaflutole | 23 | | |
| Flufenacet | | 20 | |
| Broxynil octanoate | 20.8 | | 20.8 |
| Broxynil heptanoate | 21.2 | | 21.2 |
| Acetochlor | | 26.05 | |
| Borresperse NA | 2 | 2 | 2 |
| Morwet D425 | 0.25 | 0.25 | 0.25 |
| Glycerin | 8 | 8 | 8 |
| Potassium chloride | 3 | 3 | 3 |
| Aluminum oxide | 0.2 | 0.2 | 0.2 |
| Attagel 50 | 0.15 | 0.1 | 0.1 |
| Hi Sil 233 | 0.5 | 0.2 | 0.2 |
| Antifoam 8830FG | 0.15 | 0.15 | 0.15 |
| Proxel GXL | 0.05 | 0.05 | 0.1 |
| Water | 12.7 | 16 | 16 |
| Aromatic A-150 | 5 | 20 | 5 |
| Ca DDBS | 0.5 | 1 | 0.5 |
| Ethoxylated alcohol | 2.5 | 3 | 2.5 |
| Total | 100 | 100 | 100 |
| Special gravity | 1.2 | 1.195 | 1.3 |
| Viscosity, set | 1550 | 1255 | 1340 |
| Viscosity, stirred | 250 | 150 | 310 |

TABLE 34

| Fertilizer test results | | | |
|---|---|---|---|
| 32-0-0 fertilizer + 50 mesh retain, % | 0.02 | 0 | 0 |

Example 15

A plant growth regulator cyclanilide suspension concentrate (SC) was prepared using the same procedures as detailed in Example 3 and then further mixed with the water-soluble mepiquat chloride to form a suspension solution mixture. The resultant liquid mixture surprisingly showed not only the same pattern of stability and induced shear thinning (Table 35) but also the same fertilizer compatibility (Table 36).

TABLE 35

| | 93 |
|---|---|
| Cyclanilide | 30 |
| Borresperse NA | 2.5 |
| Morwet D425 | 0.5 |
| Hi Sil 233 | 0.2 |
| Attagel 50 | 0.3 |
| Aluminum oxide | 0.4 |
| Glycerin | 10 |
| KCl | 3 |
| Water | 43.1 |
| Mepiquat chloride | 10 |
| Total | 100 |
| Particle size, micron | 2.50 |
| Specific gravity, g/ml | 1.201 |
| Viscosity, cps, set | 160 |
| Viscosity, cps, stirred | 80 |

TABLE 36

| Fertilizer test results | |
|---|---|
| 3-18-18 fertilizer + 50 mesh retain, % | 0.02 |
| 32-0-0 fertilizer + 50 mesh retain, % | 0 |
| 10-34-0 fertilizer + 50 mesh retain, % | 0 |

Example 16

Insecticide and herbicide suspension concentrates (SC) were prepared with the same procedures as detailed in Example 3, and then further mixed with emulsifiable concentrates (EC) of oil adjuvants to form resultant suspoemulsions (SE). The resultant suspoemulsion surprisingly showed the same pattern of stability and induced shear thinning (Table 37). All samples showed the same fertilizer compatibility (Table 38)

TABLE 37

| | 94 | 95 | 96 |
|---|---|---|---|
| Imidacloprid 550 SC (Sample 68) | 64 | | |
| BYI 8330 260 SC (Sample 76) | | 20 | |
| Isoxaflutole 560 SC (Sample 89) | | | 50 |
| Atlox 4914 | 4 | | |
| Agnique ME -181 U (methyl oleate) | 34.2 | | 45 |
| Atlox 4912 | 1.8 | | |
| Soprophor TS 29 | | | 5 |
| Halcomid 810 (methyl carprylate caprate) | | 76 | |
| Total | 100 | 100 | 100 |

TABLE 38

| Fertilizer test results | | | |
|---|---|---|---|
| 3-18-18 fertilizer + 50 mesh retain, % | 0 | 0 | — |
| 32-0-0 fertilizer + 50 mesh retain, % | — | — | 0.08 |

What is claimed is:

1. A fluid thixotropic fertilizer-compatible pesticidal composition substantially free of surfactants comprising:
   (a) at least one agrochemically active compound;
   (b) a metal lignosulfate salt, wherein said metal lignosulfate salt is a non-surface active dispersant;
   (c) a at least one lubricant selected from silica or alumina;
   (d) a water soluble salt of a strong acid; and
   (e) water;
   wherein the agrochemically active compound is in the form of solid particles, wherein the solid particles have an average diameter from 1 nm to 100 microns and are of a sufficiently small average diameter to be effectively dispersed in the composition and the metal lignosulfate salt and water soluble salt are present in a ratio of from about 2:1 to about 1:20 and are combined in amounts effective to disperse the particles in the water.

2. A fluid thixotropic composition according to claim 1 wherein the agrochemically active compound is an insecticide.

3. A fluid thixotropic composition according to claim 1 wherein the agrochemically active compound is a insecticide of formula (I)

$$R-N\overset{(A)}{\underset{\underset{X-E}{\|}}{\diagdown}}(Z)$$ (I)

wherein
R is hydrogen, acyl, alkyl, aryl, aralkyl, heteroaryl or heteroarylalkyl;
A is hydrogen, acyl, alkyl, aryl, or a bifunctional group that is linked to Z;
E is $NO_2$, CN, or a halogenoalkylcarbonyl group;
X is —CR'= or =N—, wherein R' is hydrogen or a bifunctional group linked to Z;
Z is alkyl, —OR", —SR", or —NR"R", or Z is a group linked to (i) the radical A or (ii) the radical X or (iii) both A and X;
provided that when E is CN, Z is not methyl and R is not a (6-chloro-3-pyridyl)methyl

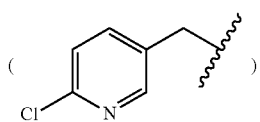 [SMILES: *Cc1ccc(Cl)nc1]
radical.
4. A fluid thixotropic composition according to claim 1 wherein the agrochemically active compound is
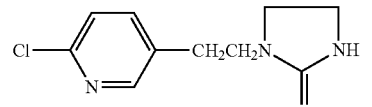
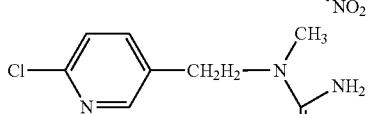
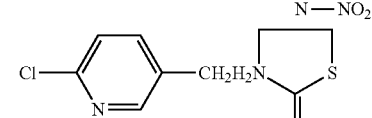
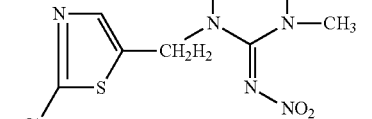
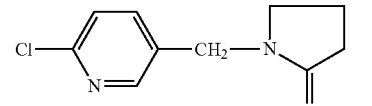
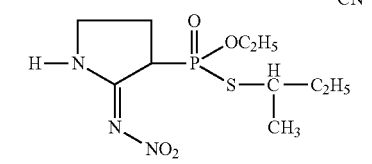
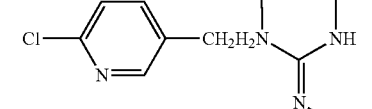
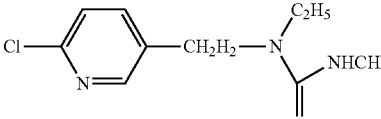
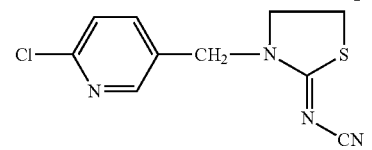
-continued
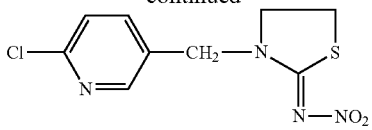
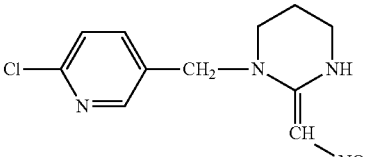
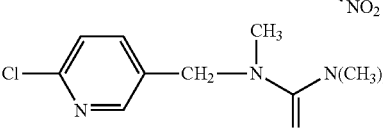
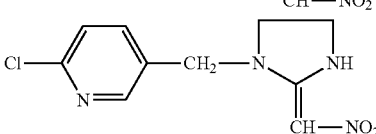
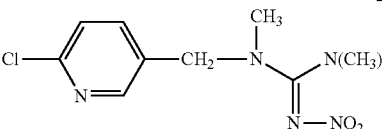
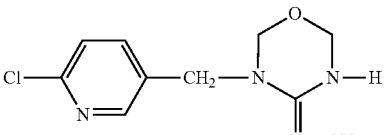
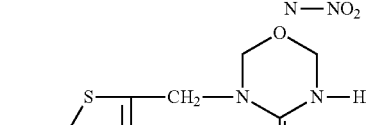
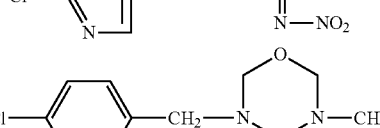
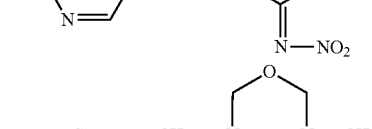
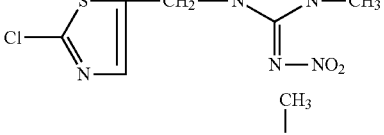
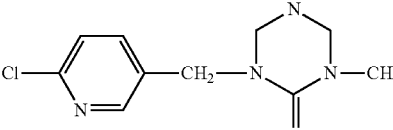
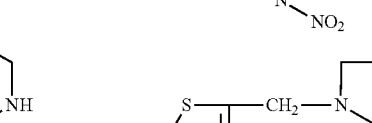

5. A fluid thixotropic composition according to claim 1 wherein the agrochemically active compound is imidacloprid, thiamethoxam, thiacloprid, clothianidin, nitenpyram, nithiazine, or dinotefuran.

6. A fluid thixotropic composition according to claim 1 wherein the agrochemically active compound is a herbicide.

7. A fluid thixotropic composition according to claim 1 wherein the agrochemically active compound is a fungicide.

8. A fluid thixotropic composition according to claim 1 wherein the agrochemically active compound is a plant growth regulant.

9. The composition of claim 1 wherein the agrochemically active compound and metal lignosulfate salt are present at a ratio of from about 60:1 to about 1:10.

10. The composition of claim 1 wherein the particles are from about 2 to 4 microns average diameter.

11. The composition of claim 1 wherein the metal lignosulfate salt is an alkali metal lignosulfate salt or an alkaline earth metal lignosulfate salt.

12. The composition of claim 1 wherein the water soluble salt of a strong acid is LiCl, NaCl, KCl, $MgCl_2$, $CaCl_2$, $FeCl_3$, $NH_4NO_3$, $Mg(NO_3)_2$, $NaNO_3$, $K_3PO_4$, $(NH4)_2SO_4$, $Na_2SO_4$, or $ZnSO_4$.

13. A product comprising a composition according to claim 1 and an agriculturally acceptable liquid fertilizer for simultaneous, separate, or sequential application for control of pests at a locus.

14. A fluid thixotropic composition of claim 1, wherein said agrochemically active compound is imidacloprid.

15. A fluid thixotropic composition of claim 1, wherein said at least one lubricant is silica and alumina.

16. A fluid thixotropic composition of claim 1, wherein said metal lignosulfate salt comprises sodium lignosulfate, potassium lignosulfate, lithium lignosulfate, or calcium lignosulfate.

17. A fluid thixotropic composition of claim 16, wherein said metal lignosulfate salt comprises sodium lignosulfate.

18. A fluid thixotropic composition of claim 1, wherein said water soluble salt of a strong acid comprises KCl.

19. A fluid thixotropic composition of claim 1 further comprising an organic sulfonate.

20. A fluid thixotropic composition of claim 19, wherein said organic sulfonate comprises ammonium salt of alkyl naphthalene sulfonate, sodium salt of alkyl naphthalene sulfonate, or calcium salt of alkyl naphthalene sulfonate.

21. A fluid thixotropic composition of claim 1, wherein
 (a) said at least one agrochemically active compound comprises imidacloprid;
 (b) said metal lignosulfate salt comprises sodium lignosulfate, potassium lignosulfate, lithium lignosulfate, or calcium lignosulfate; and
 (c) said water soluble salt of a strong acid comprises LiCl, NaCl, KCl, $MgCl_2$, $CaCl_2$, $FeCl_3$, $NH_4NO_3$, $Mg(NO_3)_2$, $NaNO_3$, $K_3PO_4$, $(NH4)_2SO_4$, $Na_2SO_4$, or $ZnSO_4$.

22. A fluid thixotropic composition of claim 1, wherein said fluid thixotropic fertilizer-compatible pesticidal composition is free of surfactants.

23. A fluid thixotropic composition free of a surfactant comprising:
   (a) an agrochemically active compound;
   (b) a metal lignosulfate salt, wherein said metal lignosulfate salt is a non-surface active dispersant;
   (c) a water soluble salt of a strong acid; and
   (d) water;
   wherein the compound is in the form of solid particles and/or liquid globules of sufficiently small average diameter to be effectively dispersed in the composition and wherein the metal lignosulfate salt and water soluble salt are combined in amounts effective to disperse the particles and/or globules in the water.

* * * * *